US011078459B2

(12) United States Patent
Tourlomousis et al.

(10) Patent No.: US 11,078,459 B2
(45) Date of Patent: Aug. 3, 2021

(54) INTEGRATED METHODS FOR PRECISION MANUFACTURING OF TISSUE ENGINEERING SCAFFOLDS

(71) Applicant: THE TRUSTEES OF THE STEVENS INSTITUTE OF TECHNOLOGY, Hoboken, NJ (US)

(72) Inventors: Filippos Tourlomousis, Hoboken, NJ (US); Robert Chang, Wayne, NJ (US); Dilhan Kalyon, Teaneck, NJ (US)

(73) Assignee: THE TRUSTEES OF THE STEVENS INSTITUTE OF TECHNOLOGY, Hoboken, NJ (US)

( * ) Notice: Subject to any disclaimer, the term of this patent is extended or adjusted under 35 U.S.C. 154(b) by 217 days.

(21) Appl. No.: 15/998,685

(22) Filed: Aug. 15, 2018

(65) Prior Publication Data

US 2019/0106674 A1 Apr. 11, 2019

Related U.S. Application Data

(60) Provisional application No. 62/545,527, filed on Aug. 15, 2017.

(51) Int. Cl.

| | |
|---|---|
| *A61K 8/00* | (2006.01) |
| *A61L 27/50* | (2006.01) |
| *C12N 5/00* | (2006.01) |
| *A61K 35/28* | (2015.01) |
| *B33Y 70/00* | (2020.01) |
| *A61L 27/38* | (2006.01) |
| *B33Y 10/00* | (2015.01) |
| *C12N 5/0775* | (2010.01) |

(52) U.S. Cl.
CPC ............ *C12N 5/0068* (2013.01); *A61K 35/28* (2013.01); *A61L 27/3834* (2013.01); *B33Y 10/00* (2014.12); *B33Y 70/00* (2014.12); *C12N 5/0662* (2013.01)

(58) Field of Classification Search
None
See application file for complete search history.

(56) References Cited

U.S. PATENT DOCUMENTS

| | | | | |
|---|---|---|---|---|
| 9,011,754 | B2 * | 4/2015 | Leong | C08J 9/00 264/465 |
| 10,780,198 | B2 * | 9/2020 | Jeffries | D01F 6/62 |
| 2020/0232121 | A1 * | 7/2020 | Finnegan | D01D 5/0023 |

OTHER PUBLICATIONS

Prager-Khoutorsky et al., Fibroblast polarization is a matrix-rigidity-dependent process controlled by focal adhesion mechanosensing 2011; Nature Cell Biology; pp. 1457-1466.*
Ristovski et al., Biointerphases , 2015, pp. 1-10; Improved fabrication of melt electrospun tissue engineering scaffolds using direct writing and advanced electric field control.*
Farooque et al., Measuring stem cell dimensionality in tissue scaffolds Biomaterials 35 (2014) 2558-2567.*
Tourlomousis et al., 2019; Machine learning metrology of cell confinement in melt electrowritten threedimensional biomaterial substrates Microsystems & Nanoengineering volume; pp. 1-19.*
Hochleitner et al., Biofabrication 2015; pp. 1-10; Additive manufacturing of scaffolds with sub-micron filaments via melt electrospinning writing.*
Hutmacher et al., Mechanical properties and cell cultural response of polycaprolactone scaffolds designed and fabricated via fused deposition modeling; 2001 John Wiley & Sons, Inc. pp. 203-216.*
Stevens, et al., "Exploring and Engineering the Cell Surface Interface", Science, vol. 310, Nov. 18, 2005, pp. 1135-1138.
Kumar, et al., "The determination of stem cell fate by 3D scaffold structures through the control of cell shape", Biomaterials, vol. 32, Sep. 3, 2011, pp. 9188-9196.
Tourlomousis, et al. "Melt Electrospinning Writing Process Guided by a 'Printability Number'", Journal of Manufacturing Science and Engineering, vol. 139, Aug. 2017, pp. 081004-1-081004-15.
Groll, et al., "Biofabrication: reappraising the definition of an evolving field", Biofabrication, vol. 8, Jan. 8, 2016, pp. 1-5.
Filiano, et al., "Unexpected role of interferon-γ in regulating neuronal connectivity and social behaviour", Nature, vol. 535, Jul. 21, 2016, pp. 425-429 and 13 pages of Extended Data.
McKee, et al., "Advances and challenges in stem cell culture", Colloids and Surfaces B: Biointerfaces, vol. 159, Jul. 27, 2017, pp. 62-77.
Bartosh, et al., "Aggregation of human mesenchymal stromal cells (MSCs) into 3D spheroids enhances their antiinflammatory properties", PNAS, vol. 107, No. 31, Aug. 3, 2010, pp. 13724-13729.
Guilak, et al., "Control of Stem Cell Fate by Physical Interactions with the Extracellular Matrix", Cell Stem Cell, vol. 5, Jul. 2, 2009, pp. 17-26.
McBeath, et al., "Cell Shape, Cytoskeletal Tension, and RhoA Regulate Stem Cell Lineage Commitment", Developmental Cell, vol. 6, Apr. 2004, pp. 483-495.

(Continued)

*Primary Examiner* — Maria G Leavitt
(74) *Attorney, Agent, or Firm* — Lewis Roca Rothgerber Christie LLP

(57) ABSTRACT

Methods for the development and integration of multiple apparatuses and methods for achieving administration of stem cell therapies include precision manufacturing of tissue scaffolds and/or bioreactor substrates. The nano/microscale fiber material extrusion typifying the electrospinning process is married with the fiber alignment and layering characteristic of an additive manufacturing process. The method generates porous fibrous 3-D meshes with precision controlled structures from biopolymer melts and solutions and gels, blends, and suspensions with and without cells. A method of tracking the migration histories and shapes of stem cells on scaffold surfaces relies on immunofluorescent imaging and automated algorithms based on machine learning. The combination of the precision manufacturing method and the method of cell tracking and cell shape statistics, along with understanding of the intimate relationship between the cell shape/phenotype and scaffold architecture leads to an integrated method for cultivating and harvesting cells having desired phenotypes.

16 Claims, 34 Drawing Sheets
(18 of 34 Drawing Sheet(s) Filed in Color)

(56) References Cited

OTHER PUBLICATIONS

Thomas, et al., “Engineering gene expression and protein synthesis by modulation of nuclear shape”, PNAS, vol. 99, No. 4, Feb. 19, 2002, pp. 1972-1977.

* cited by examiner

B) Free Flow Spinline Regime

Stationary Collector Plate

Moving Collector Plate $N_{PR,2}^{*} = 31.9$ $N_{PR,2}^{*} = 57.63$ $N_{PR,2}^{*} = 106$ $N_{PR,2}^{*} = 106$

FLAT

FLAT

FLAT

FLAT

MEW | 0-90°

MEW | 0-90°

MEW | 0-45°

MEW | 0-45°

Cellular Scale

Cell Body

Sub-cellular Scale

Nucleus Body

Sub-cellular Scale

Focal Adhesions

INTEGRATED METHODS FOR PRECISION MANUFACTURING OF TISSUE ENGINEERING SCAFFOLDS

CROSS-REFERENCE TO RELATED APPLICATION

This application claims priority to U.S. Provisional Patent Application Ser. No. 62/545,527 filed Aug. 15, 2017, the entire disclosure of which, including the specification, drawings, Attachment A, and Attachment B, is incorporated herein by reference.

STATEMENT REGARDING FEDERALLY SPONSORED RESEARCH

This invention was made with government support under Grant No. CMMI-MME-1554150 awarded by the National Science Foundation. The government has certain rights in the invention.

FIELD OF THE INVENTION

The invention disclosed herein relates to the fields of additive manufacturing, tissue engineering, scaffold and bioreactor design and fabrication, regenerative medicine, stem cell expansion, stem cell differentiation, stem cell population homogeneity and heterogeneity, and automated image-based screening methods for the classification of stem cell phenotypes.

BACKGROUND OF THE INVENTION

The current understanding in stem cell expansion and differentiation, generally demonstrated on two-dimensional ("2-D") substrates, is that it is necessary to change the stiffness of the substrate and/or include one or more bioactive reagents (typically cocktails) so that the phenotype of the stem cells can be conserved or modified during the expansion and differentiation of stem cells in regenerative therapies. Overall, the yields are relatively low and there are significant issues of maintaining the purity and homogeneity of the stem cell populations. The known methods for screening phenotypes of the stem cells (e.g., ELISA or flow cytometry) rely on bulk measurements and the use of relatively large stem cell populations. Thus, there are myriad issues in the current state of regenerative medicine using stem cells.

SUMMARY OF THE INVENTION

Embodiments of the invention disclosed herein include one or more methods that can be integrated to implement regenerative stem cell based therapies. The methods can be implemented under known paradigms, or may be integrated to implement new paradigms or approaches to regenerative stem cell based therapies.

A first embodiment of the present invention includes a first method ("Method 1") for precision manufacturing of three-dimensional ("3-D") biomaterial scaffolds with precisely tunable porous microarchitectures and geometrical feature sizes at the cell's operating length scales (10-100 μm). This dimensional scale window of precisely controllable microscale geometrical feature sizes is unattainable with other polymer melt based additive manufacturing technologies such as, for example, fused deposition modeling (widely known as "3-D printing"). In embodiments of the method, high-fidelity fibrous scaffolds are fabricated through electrohydrodynamic (EHD) printing of a biopolymer melt using a melt electrowriting ("MEW") technique. Embodiments of the method are used to generate porous fibrous 3-D scaffolds with precision-controlled porous microarchitectures from biopolymer melts. In exactly the same way, embodiments of the method can be used to generate 3-D scaffolds from a wide range of alternate materials such as polymer solutions, gels, blends and suspensions with and without cells. In embodiments, the scaffolds are, or are component parts of, devices such as static tissue engineered models and/or dynamic tissue engineered models embedded within perfusable bioreactors.

A second embodiment of the present invention includes a second method ("Method 2") for tailoring scaffold designs for stem cell expansion so that the stem cell phenotype is not altered. Embodiments of the method are used for homogeneous stem cell expansion without the presence of any cell-instructive chemicals and/or bioactive molecules and/or growth factors.

A third embodiment of the present invention includes a third method ("Method 3") for tailoring scaffold designs for stem cell expansion and subsequent targeted differentiation of the stem cell phenotype. Embodiments of the method are used for homogeneous stem cell expansion and subsequent targeted differentiation without the presence of any cell-instructive chemicals and/or bioactive molecules and/or growth factors.

A fourth embodiment of the present invention includes a fourth method ("Method 4") for machine learning based classification of stem cell phenotypes using methods (e.g., immunofluorescent imaging) for tuning manufacturing protocols for reproducible harvesting of targeted stem cell populations. This advanced manufacturing approach is biologically qualified with a metrology framework that models and classifies cell confinement states under various substrate dimensionalities and architectures.

BRIEF DESCRIPTION OF FIGURES

The patent or application file contains at least one drawing executed in color. Copies of this patent or patent application publication with color drawing(s) will be provided by the Office upon request and payment of the necessary fee.

For a more complete understanding of the present invention, reference is made to the following detailed description of an exemplary embodiment considered in conjunction with the accompanying figures, in which:

FIG. 21's Scaffold's configuration is designated as MEW|0-90° and that of scaffold D is designated as MEW|10-45°.

FIGS. 31-38 are multiple sets of photographic immunofluorescence images illustrating the expansion of stem cells using conventional expansion methods employing flat surfaces, wherein FIGS. 31 and 32 show positive marker expression, FIGS. 35 and 36 show no negative marker expression after 1 day of culture, FIGS. 33 and 34 show positive marker expression and FIGS. 37 and 38 show negative marker expression after 7 days of culture, the photographic images illustrating that stem cells lose their characteristic phenotype within one week of culturing, thus significantly decreasing their expansion potential and introducing problems with control of the purity and homogeneity of the stem cell population;

FIG. 86 is a grayscale maximum projection of the red channel cell body image overlaid with the contour of the segmented cell body, FIG. 87 is a grayscale maximum projection of the blue channel image overlaid with the contour of the segmented nucleus, and FIG. 88 is a grayscale maximum projection of the green channel image overlaid with the contour of the segmented focal adhesions (scale bar: 20 μm);

FIGS. 89-97 illustrate an algorithmic procedure according to an embodiment of the present invention that allows the development of critical cellular and subcellular focal adhesion morphometric and distribution metrics that are useful for the training and application of the developed classification method to various cell types according to an embodiment of the present invention;

DETAILED DESCRIPTION OF THE INVENTION

Figure 1:
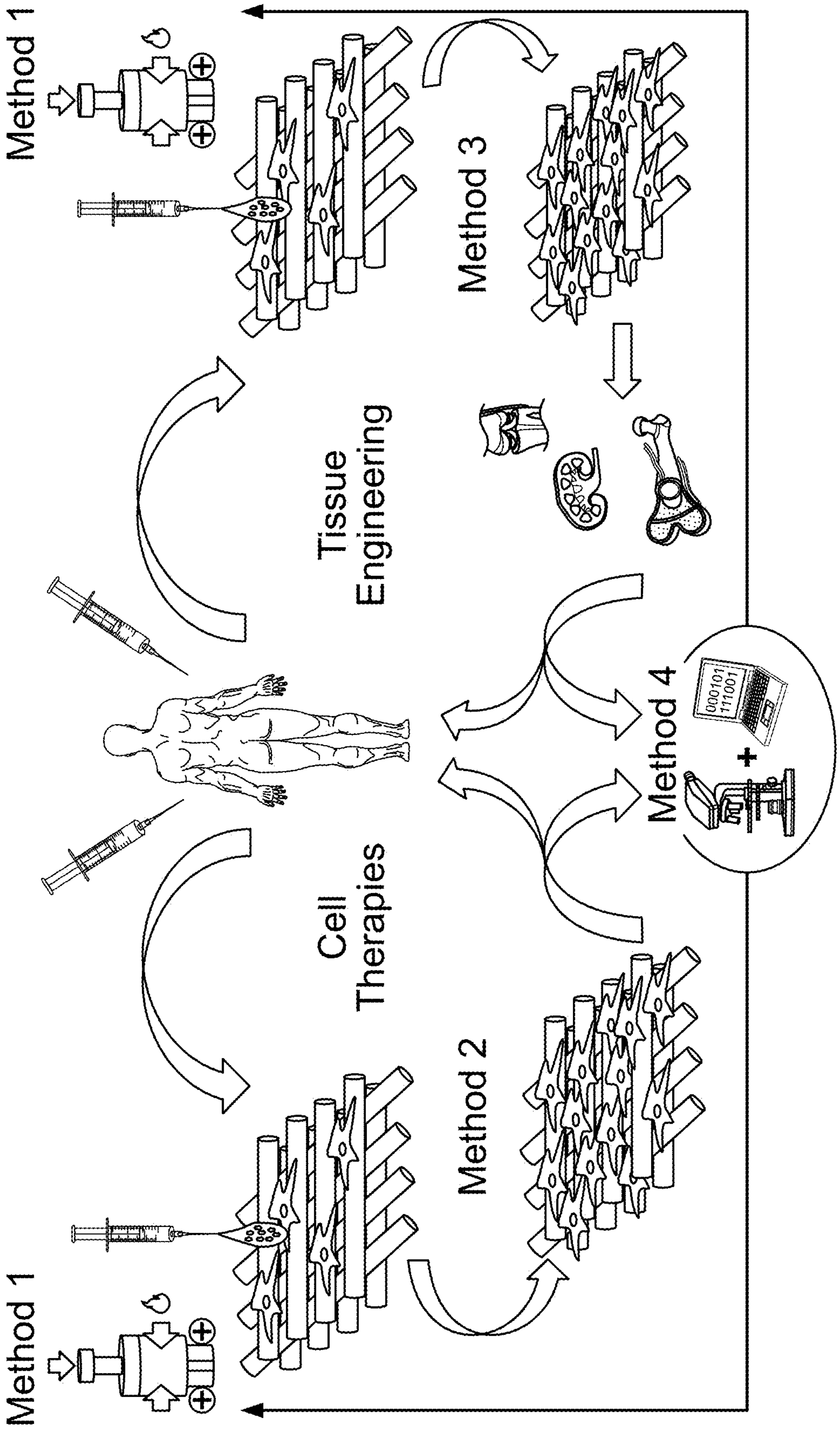
FIG. 1 is a schematic diagram presenting an overview of a conceptual integration of Method 1, Method 2, Method 3, and Method 4 according to an embodiment of the present invention.
Figure 2:
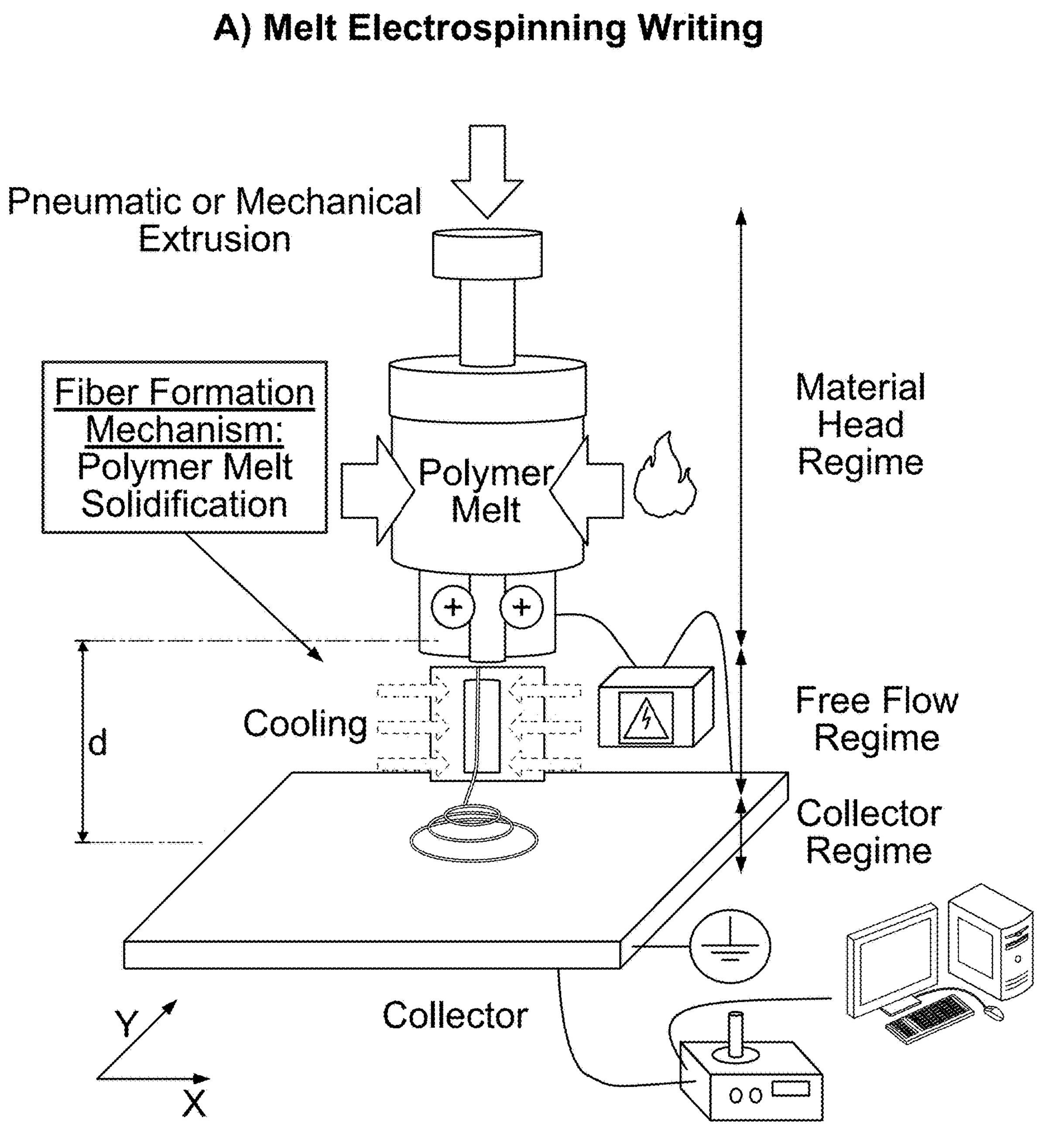
FIG. 2 is a schematic diagram illustrating a melt electrowriting apparatus according to an embodiment of the present invention.
Figure 3:
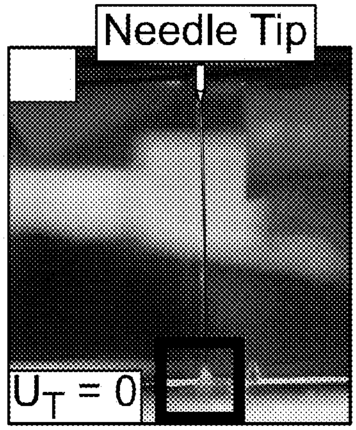
FIGS. 3-7 are a set of reproductions of photographic images depicting the polymer melt jet formed between the charged needle tip and the grounded aluminum collector, the process regime known as free flow spinline regime, according to embodiments of the present invention.
Figure 4:
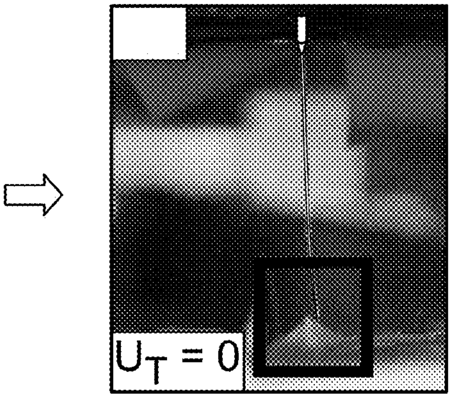
Figure 5:
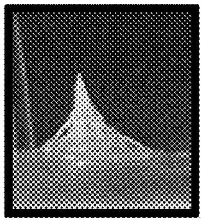
Figure 6:
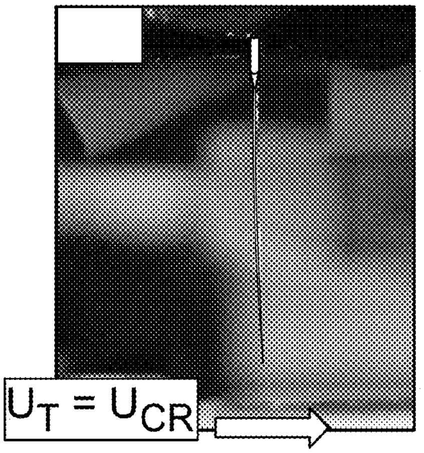
Figure 7:
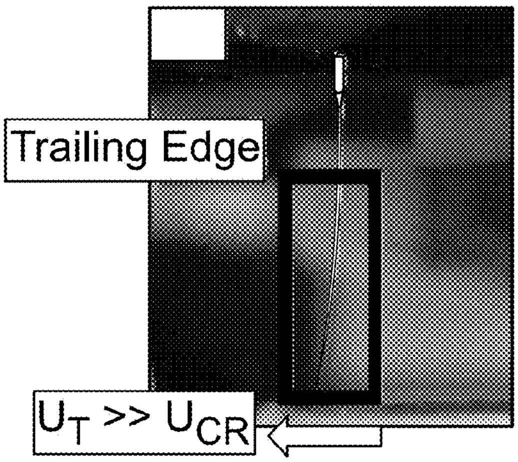
Figure 8:
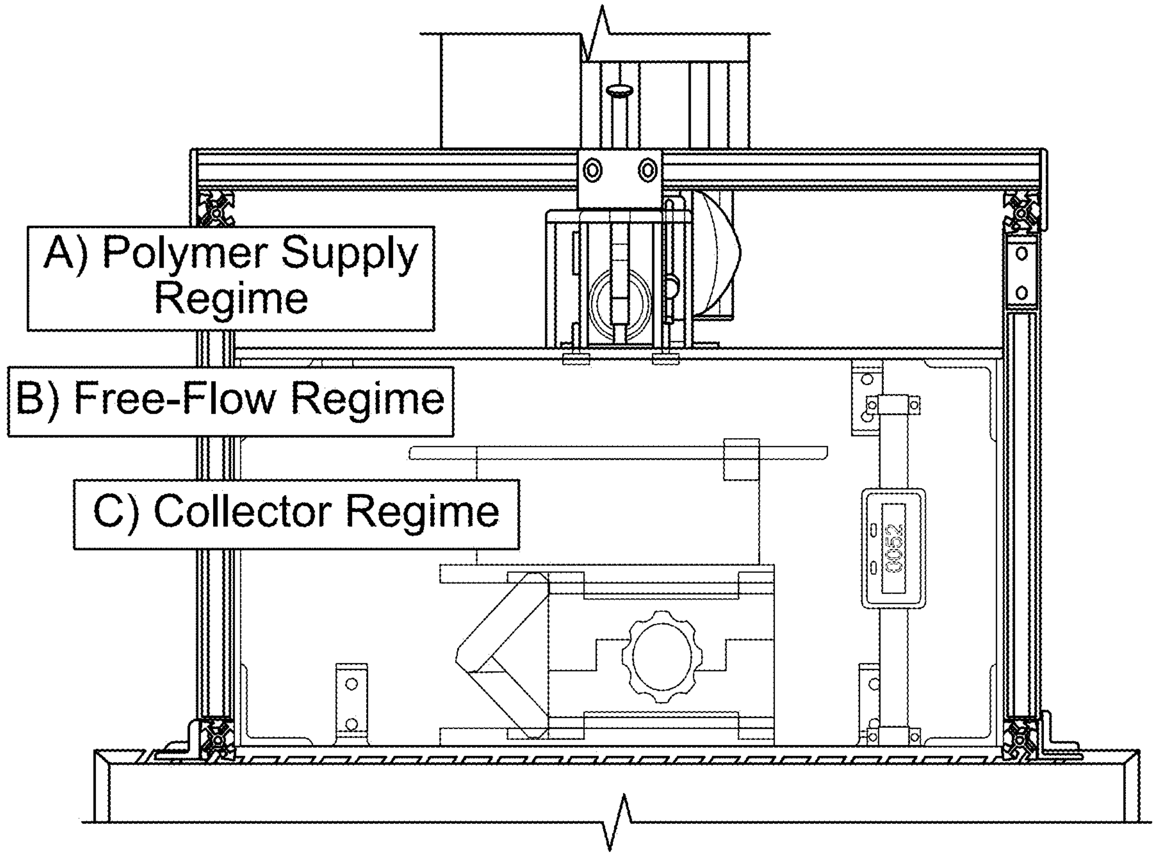
FIG. 8 is a schematic diagram depicting a custom built manufacturing system, according to an embodiment of the present invention.

Previously-known stem cell based therapies rely on the harvesting of stem cells from the patient, followed by expansion of the cell number in a bioreactor system. Typically, this is achieved in conjunction with subsequent direct and localized delivery (e.g., injection or infusion) of stem cell suspensions through various access routes that home to the site of tissue injury. An alternative mode of stem cell delivery for enhanced cell engraftment and survival entails seeding the expanded stem cells on bioresorbable scaffolds with subsequent implantation of the tissue constructs to the targeted site of tissue injury. Prior to the invention of the methods and structures disclosed herein and further embodiments thereof, there has been no extant sophistication of the design criteria for the bioreactor substrate and scaffold geometries needed to achieve high expansion rates while conserving the undifferentiated state of the stem cells (e.g., original phenotype or "sternness"), or of achieving a particular terminal differentiation state (e.g., tissue-specific function) of the stem cells. Conserving the functional homogeneity of the stem cell population (i.e., avoiding functional heterogeneity of the population) to be administered into the body of the patient is another issue resolved by embodiments of the present invention.

Embodiments of the present invention provide new methodologies for improving the homogeneity during stem cell expansion, long-term in vitro differentiation, and phenotype screening and targeting in ways that provide novel and unexpected results. The elements of the invention are first instructed by the discoveries disclosed herein that demonstrate an intimate relationship between the geometry of the engineered bioreactor or scaffold and the manner in which stem cells expand and differentiate. It is disclosed that stem cells seeded on 3-D substrates generate different types and distributions of stem cell shapes and phenotypes in comparison to their 2-D surface counterparts. Furthermore, it is disclosed herein that the particular 3-D pore geometry has a profound effect on stem cell shape and the associated stem cell differentiation states. For instance, normal human dermal fibroblasts (NHDFs) were grown on 3-D MEW scaffolds with 0-90° architecture (MEW|10-90°) scaffolds and on 3-D MEW scaffolds with 0-45° architecture (MEW|0-45°) scaffolds. Compared to a 2-D petri dish control, both scaffolds demonstrate more uniform cell shapes. The former scaffold confined the cells in a two-dimensional space, while the latter scaffold put them in a 3-D confined and suspended state. Motivated by this, stem cells that behave morphologically similarly to NHDFs were cultured on 3-D MEW fibrous scaffolds demonstrating preservation of their stem cell phenotype significantly longer compared to 2-D conventional flat culture substrates.

As disclosed herein, a new manufacturing method according to an embodiment of the present invention allows precise control of the porous microarchitecture of a 3-D scaffold with cellular-relevant geometrical feature sizes, providing control of the shapes and the phenotypes of the expanded stem cells. Embodiments of the present invention include a method to generate the desired types of scaffold geometry in a reproducible and industrially scalable manner. Such embodiments of the present invention combine melt electrospinning and additive manufacturing. Embodiments of this manufacturing method (designated hereinafter as "the TCK method") are used to fabricate scaffold meshes of geometrical fidelity and precision not encountered previously. Embodiments of the TCK method are used to fabricate novel scaffold designs involving, for example, 0-90 and 0-45 degree fibrous architectures with consistent fiber diameters, orientations, alignment, and interconnectivities.

The TCK method utilizes Melt Electrospinning Writing (MEW) to manufacture the integrated scaffolds. In one embodiment, Poly(e-polycaprolactone) (PCL) is selected for MEW on the basis of its Food and Drug Administration approval for in vivo applications, biocompatibility, long-term biodegradability, and relatively low and wide melt processing temperature window (60°-90° C.). PCL material specifications with an average molecular weight of 45,600 g/mol and polydispersity of 1.219 can be used. Such can be obtained, for example, from Perstorp Ltd. of Warrington, UK (Capa6500).

PCL pellets are molded into 8 mm and 25 mm circular disks using aluminum shims between Teflon surfaces and a Carver press at 120° C. for subsequent rheological characterization. This can be accomplished with the advanced rheological extended system (ARES) of Rheometric Scientific (currently TA Instruments) in conjunction with stainless-steel parallel disk fixtures with 25 mm diameter for small-amplitude oscillatory shear (SAOS) and steady torsional flow experiments. The force-rebalance transducer of the rheometer is capable of measuring simultaneously both the normal force and the torque. The oven temperature of the rheometer is controlled within ±0.1° C. The rheological characterization experiments can be carried out at 70° C., 80° C., and 90° C. and using a constant 1 mm gap.

A high-resolution heat-assisted MEW system configuration can be established. The process design is guided by detailed characterization of the thermorheological processing properties of the biomaterial substrate along with the fluid dynamics, heat transfer, and electrostatics multiphysics phenomena governing the process under investigation. The overall system configuration is analyzed based on three defined discrete process regimes.

First, the polymer melt supply regime can be composed of a glass Luer-lock 5 ml syringe (such is available for purchase from Hamilton, Reno, Nev.) and a stainless-steel needle tip with a plastic hub (such as that obtainable from McMaster Carr, Elmhurst, Ill.) attached to it. The polymer melt can be maintained in a uniform melt state using an industrial heat gun (e.g., Steinel, HG 2510 ESD). In addition, a programmable syringe pump (such as that obtained from Harvard Apparatus, Holliston, Mass.) is mounted vertically and used to set the volumetric flow rate by adjusting the speed of the plunger within a syringe (flow accuracy being within 0.25% and reproducibility being within 0.05%). The temperature can be monitored both at the syringe barrel and the capillary tip with an infrared FLIR thermal camera (such as the PM 290, Inframetrics, Thermacam). In the free-flow regime, a high-voltage source (a suitable source can be acquired from Gamma High Voltage Research, Ormond Beach, Fla.) is used for the application of a voltage potential between the needle tip and a grounded electrically conductive collector. An aluminum collector is mounted on an x-y programmable stage (such as that obtainable from ASI Applied Scientific Instrumentation, Eugene, Oreg.) that is sequentially mounted on a lab jack (obtained, e.g., from Newport Corporation, Irvine, Calif.) (See FIGS. 8-13). The distance between the tip and the collector plate can be monitored using a vertical digital meter (FIGS. 8-13) and set manually using the lab jack's turning knob with a vertical positioning resolution of 0.5 mm. To compensate for ambient conditions that might affect the process, the overall system configuration is placed on an antivibrating optical table with the spinning apparatus contained within a plexiglass enclosure. Furthermore, the temperature and humidity values within the enclosure can be monitored using a multimeter (such as that which can be acquired from Extech Instruments, Waltham, Mass.) equipped with a type K thermocouple.

Figure 12:
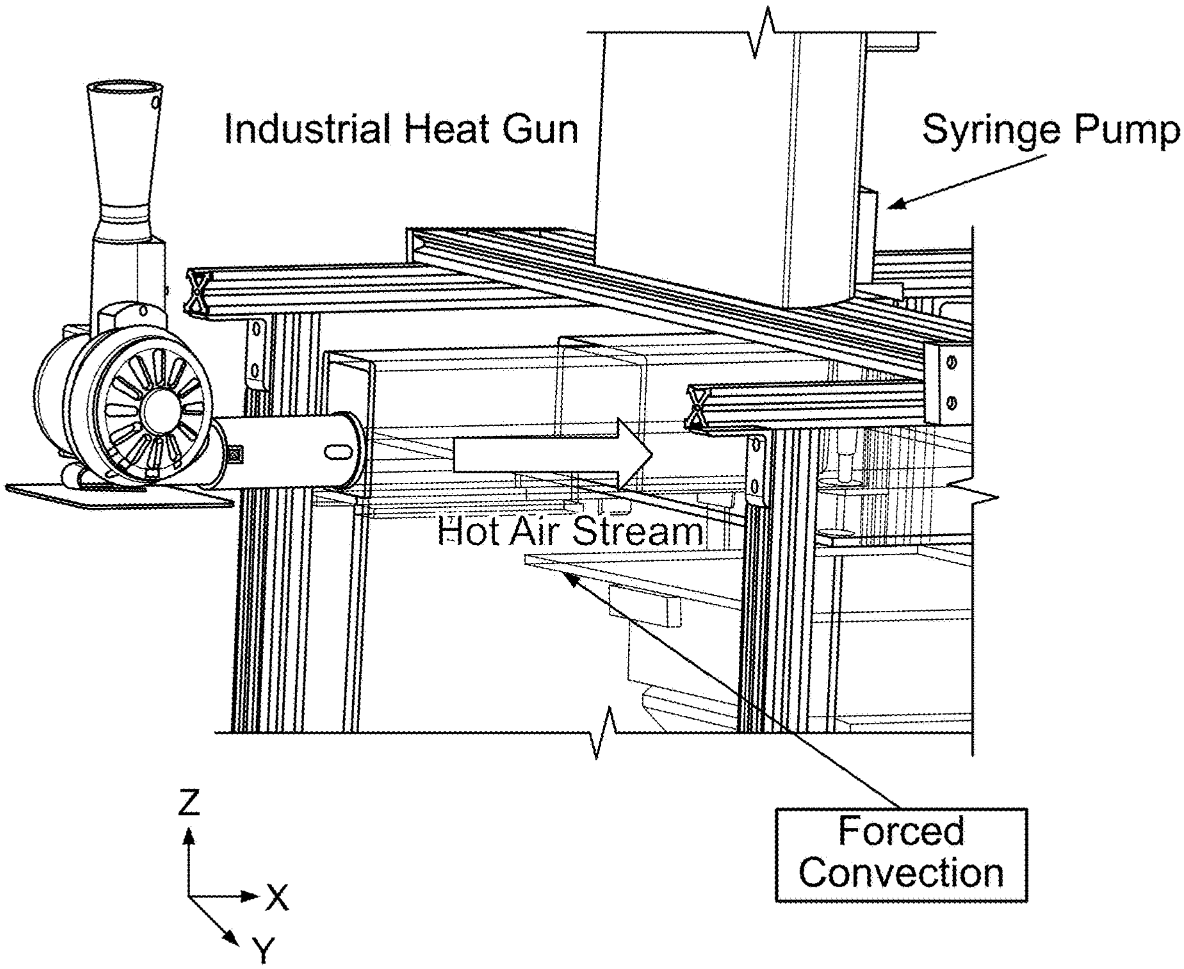
FIG. 12 is a schematic illustrating the proposed heating element.
Figure 13:
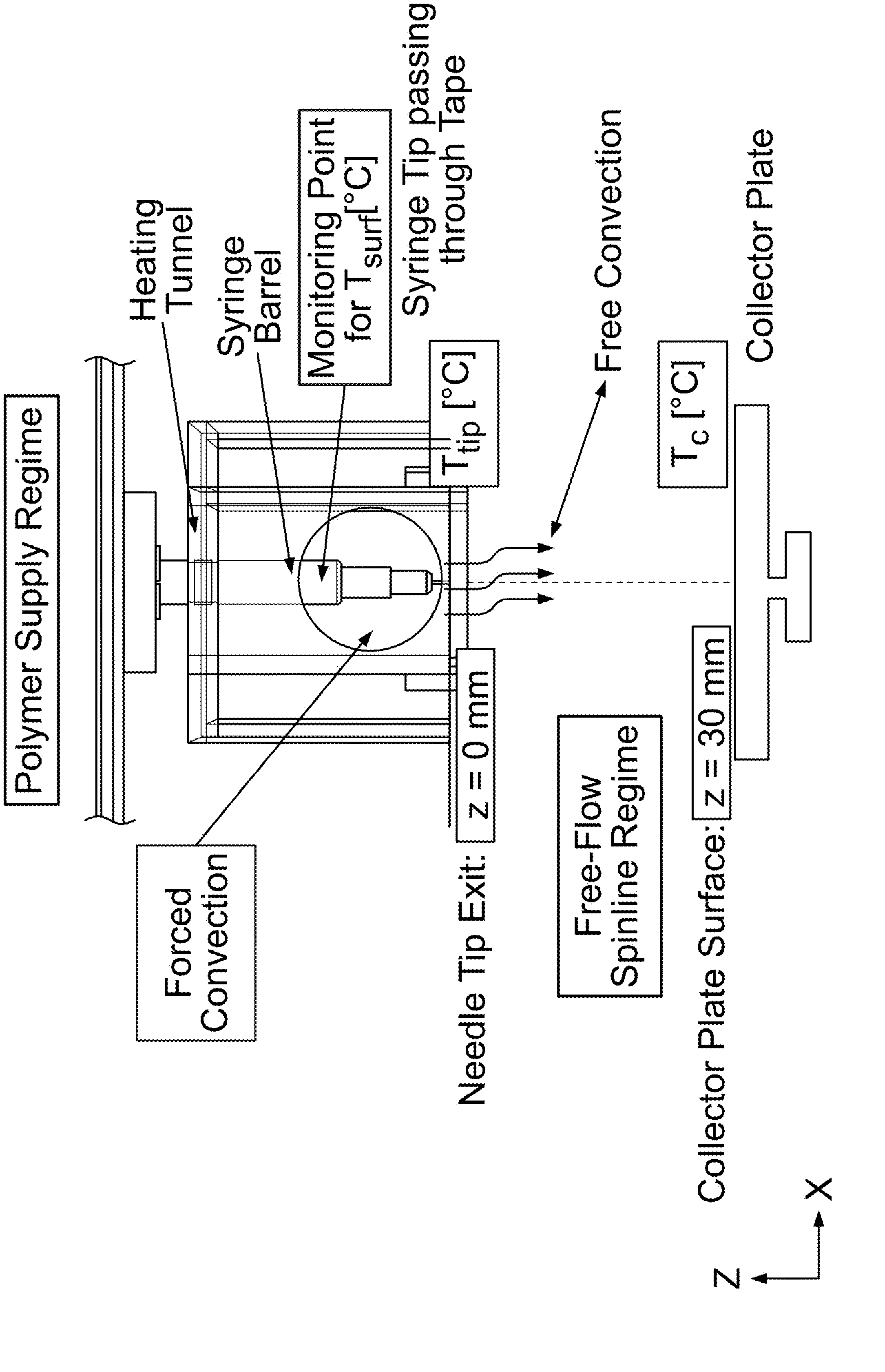
FIG. 13 is a schematic illustrating the key heat transfer mechanisms in the polymer melt supply and free-flow regime.

The heating element is composed of an industrial heat gun (HG) with controllable air flow (QHG) (0.002-0.008 $m^3$/s) and adjustable air temperature (THG) settings (49°-649° C.). The heat gun is mounted at the entrance of a heating tunnel housed by a transparent chamber constructed out of poly (methyl methacrylate) (FIG. 12). The syringe passes through the heating tunnel, and a small portion of the syringe needle tip reaches the interior of the chamber through an electrically conductive tape covering a circular opening created at the ceiling of the chamber. Heating insulation tapes are applied onto the back wall and the floor of the heating tunnel in order to minimize heat losses. The area of the circular opening covered by the tape is kept tightly sealed in order to avoid disturbances along the spinline regime from the hot stream air.

Figure 9:
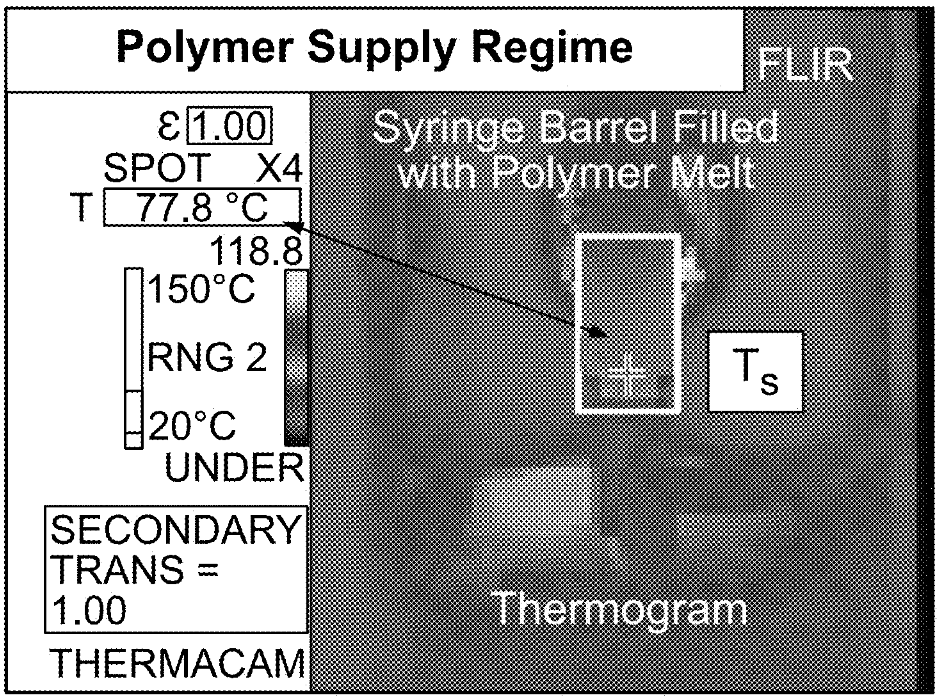
FIG. 9 is a screen-capture image of a thermogram and associated data display depicting the custom built manufacturing system.
Figure 10:
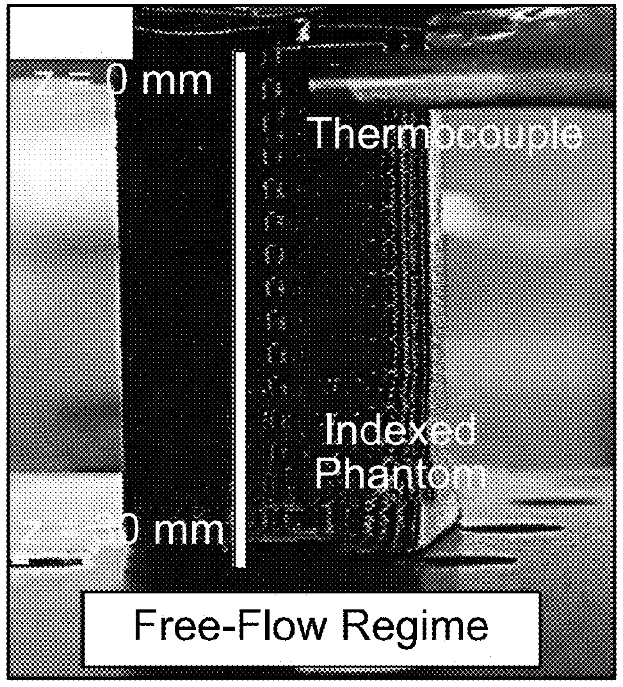
FIG. 10 is a reproduction of a photographic image of a portion of the custom built manufacturing system.

The surface of the syringe is heated due to heat transfer via forced convection generated by the heat gun, and the ambient temperature conditions along the spinline are governed by free convection through to the heated tape. The heat transfer conditions are calibrated so that the temperature at the surface of the syringe hosting the PCL melt is maintained as the desired temperature. For example, it is determined that for the air flow rate of $Q_{HG}$=0.0017 $m^3$/s and air temperature of $T_{HG}$=132° C., the temperature on the syringe surface (Ts) is set and maintained at 78±1° C. (FIG. 9). Thermal imaging using the FLIR camera confirms that the temperature at the surface of the syringe does not vary outside of the Ts±1° C. over the time course.

Figure 11:
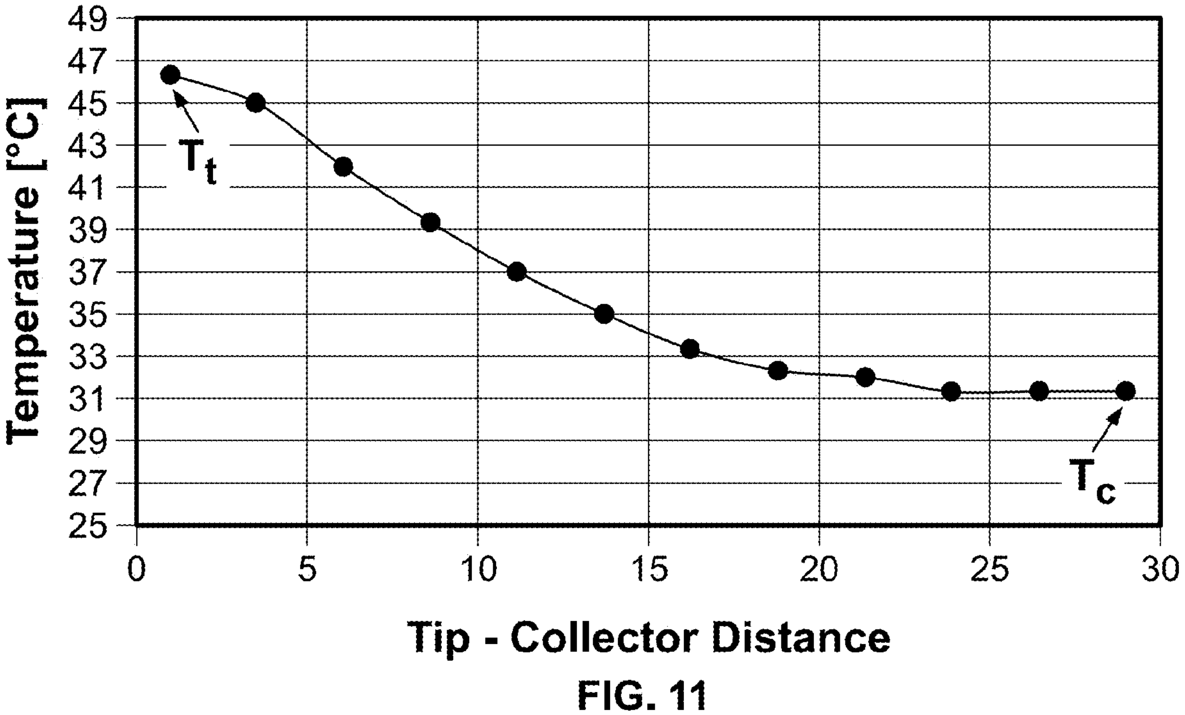
FIG. 11 is a graph of the operating centigrade temperature of the custom built manufacturing system as a function of the distance between the tip and the collector.

Thermocouple measurements along the spinline coordinate z (FIG. 10), where z=0 mm is considered a measurement point under the tip (Tt=40±5° C.) and z=30 mm is considered a measurement point on the surface of the collector plate (Tc=30±5° C.), demonstrate the presence of an exponentially decaying temperature profile (FIG. 11). Due to the high thermal conductivity of glass and the small volume of polymer melt hosted in the syringe barrel, it is assumed that the temperature of the polymer melt ($T_o$) becomes equal to $T_s$, and the system reaches thermal equilibrium after 1 h. The latter is also confirmed by measuring a stable spinline temperature profile regularly after the heat gun is set over the time course of 2 h. In this way, the presence of temperature gradients higher than 5° C. along the process regimes that may yield variations in the temperature-dependent polymer viscosity, and thus in the flow field along the process regimes, are avoided.

Although studies that have used heated air systems have reported that the temperature at the spinneret may be difficult to control accurately using this approach, the present study demonstrates that a heat-gun based system is capable of maintaining uniform heating within the material head and a spinline temperature profile, whose higher end can be set close to the onset crystallization temperature of PCL. This capability can offer an alternative way of printing aligned fibers with submicron diameter by tuning the spinline temperature so as to induce prolonged stretching, through delayed "in-flight" fiber solidification.

Prior to the printing, pure PCL pellets are loaded into a glass syringe (Hamilton). Then, the syringe is placed in a laboratory convective oven and heated for 24 h to remove any bubbles that may affect the process stability and downstream structural formability of the melt electrospun fibers. After assuring the homogeneity of the polymer melt, a needle tip at a prescribed nominal inner diameter (21 gauge—0.514 mm) is adapted onto the syringe. The syringe with the attached tip is then placed in the material head of the system, which is preheated at a temperature ($T_{surf}$=77.8° C.) with the heating element. At least 1 h is given to the system prior to initiating the printing studies in order to reach thermal equilibrium.

Thin glass coverslips are taped on the grounded aluminum plate and used as collectors for all the printing tasks. In this way, the structural formability in terms of diameter and quality of the MEW fibers can be characterized using bright field microscopy. An inverted motorized microscope (such as the IX83 from Olympus in Tokyo, Japan) along with image processing software (CELLSENS 2.11) can be used to image and characterize all samples. The fiber diameter can be measured directly from the acquired images at five different points along the length of each fiber for statistical significance, and an average fiber diameter along with its standard deviation can be recorded. The apparent pore size is determined as the average value of the circle diameters that could be fitted inside each scaffold pore. All measurements are done using a 20× objective lens with the magnification set at 12.6.

The identification of relevant dimensionless groups can be carried out using a classical dimensional analysis technique starting with process and system-specific independent parameters. The following definitions are employed. "n" is the number of independent variables relevant to the process. "j" is the number of base dimensions found in the n variables. "j" is the number of variables necessary to be considered simultaneously. "k" is the number of the independent Π terms that can be identified to describe the process and is equal to n−j (k=n−j).

The total number of independent variables, n, is equal to 12. Table 1 enumerates these variables and their base dimensions, where M stands for mass (SI unit: kilogram), L stands for length (SI unit: meter), T for time (SI unit: second), Θ for temperature (SI unit: Kelvin), and A for electric current (SI unit: Ampere).

TABLE 1

| List of independent variables along with base dimensions: j = {L, M, T, A, Θ} | | | | | | | | | | | | |
|---|---|---|---|---|---|---|---|---|---|---|---|---|
| Variables | $R_o$ | d | Q | $V_p$ | $T_t$ | $T_o$ | ρ | η | ε | γ | λ | g |
| SI units | m | m | $m^3/s$ | V | K | K | $kg/m^3$ | Pa · s | $\frac{F}{m}$ | $\frac{N}{m}$ | s | $kg/m^3$ |
| Equivalent with more basic SI units | — | — | — | $kg\ m^2s^{-3}A^{-1}$ | — | — | — | $m\ kg\ s^{-1}$ | $s^4A^2kg^{-1}m^{-3}$ | $kg\ s^{-2}$ | — | — |
| Base dimensions | L | L | $L^3T^{-1}$ | $ML^2T^{-3}A^{-1}$ | Θ | Θ | $ML^{-3}$ | $L^{-1}MT^{-1}$ | $T^4A^2M^{-1}L^{-3}$ | $MT^{-2}$ | T | $LT^{-2}$ |

This number of base dimensions is equal to 5 with j'={L, M, T, A, Θ}. Next, j is determined by assuming that j=j' and scanning for j repeating variables which do not form a dimensionless product. The prescribed number of five independent variables leads to the following independent variables j={d, Q, $V_p$, $T_t$, γ}. Thus, the number of independent dimensionless Π terms that could be formed would be equal to k=n−j=12−5=7. The following step consists of the $\Pi_i$, i=1, 2, 7 term formation. Each term is formed by forming a power product of the j repeating variables with the additional variable.

The procedure followed for P1 term formation is shown:

$$\Pi_1=R_o^{a1}g^{a2}\varepsilon^{a3}T_t^{a4}\gamma^{a5}\eta_p^{-1} \quad (1)$$

Then, the dimensions of the various quantities are inserted inside Eq. (1)

$$\text{dimension of } \Pi_1=L^{a1+a2-3a3}M^{-a3+a5-1}T^{-2a2+4a3-2a5+1}A^{2a3}\Theta^{a4} \quad (2)$$

To obtain a dimensionless parameter Π, each exponent M, L, T, etc., to needed vanish, thereby yielding a system of linear algebraic equations $$a_1+a_2-3a_3=0 \quad (3)$$

$$-a_3+a_5=1 \quad (4)$$

$$-2a_2+4a_3-2a_5=-1 \quad (5)$$

$$2a_3=0 \quad (6)$$

$$a_4=0 \quad (7)$$

TABLE 2

| List of dimensionless $\Pi_i$, i = 1, 2 . . . , 7 terms | | | | | | |
|---|---|---|---|---|---|---|
| $\Pi_1$ | $\Pi_2$ | $\Pi_3$ | $\Pi_4$ | $\Pi_5$ | $\Pi_6$ | $\Pi_7$ |
| $\frac{d^{1/2}\gamma}{g^{1/2}\eta_p}$ | $\frac{T_t}{T_c}$ | $\frac{R_o}{d}$ | $\frac{d^{5/2}g^{1/2}}{Q}$ | $\frac{g\varepsilon^{1/2}V_p}{d^{3/2}\gamma^{3/2}}$ | $\frac{d^{1/2}}{g^{1/2}\lambda}$ | $\frac{\gamma}{d^2dp}$ |

The solution of the system (Eqs. (3)-(7)) and its subsequent substitution in Eq. (1) yields a dimensionless term $\Pi_i$ shown in Table 2. The same procedure is followed for the formation of the remaining $\Pi_i$ terms shown in Table 2. Thus, the product combination of the $\Pi_i$ dimensionless terms can lead to a single dimensionless number Π

$$\Pi=\Pi_1*\Pi_2*\ldots*\Pi_7 \quad (8)$$

Substituting for each individual Pi term from Table 2 yields the following dimensionless H number, denoted as $N_1$ herein:

$$N_1=\frac{y^{1/2}\varepsilon^{1/2}}{g^{1/2}}\frac{T_t}{\lambda\rho}\frac{R_o}{Tc}\frac{V_p}{dQn_p} \quad (9)$$

To account for the translational stage speed $U_T$ as an independent parameter, an additional dimensionless group $\Pi_s$ is formulated as an additional multiplier in Eq. (8)

$$\Pi_8=\frac{U_T}{R_o^{1/2}g^{1/2}} \quad (10)$$

yielding the following $N_2$ term:

$$N_2=\frac{y^{1/2}\varepsilon^{1/2}R_o^{1/2}}{g\lambda\rho}\frac{T_t}{T_C}\frac{V_pU_T}{dQn_p} \quad (11)$$

The formulation and calculation of two separate terms, $N_1$ and $N_2$, in turn enable the investigation of printability when the process is performed under a stationary ($U_T$=0) and a moving collector ($U_T$>0), respectively. In the former case, the $N_1$ term is a function of the independent process parameters that govern the polymer melt jet formation in the free-flow regime. In the latter case, the $N_2$ term additionally accounts for the translational stage speed ($U_T$), a process variable that quantitatively affects the fiber topography on the receiving substrate. To be sure, the initial $N_1$ term is defined for the preliminary procedural step of identifying the equilibrium state conditions in the free-flow regime to ensure stable jet formation. In the absence of this preliminary step, the direct application of $N_2$ for a stationary collector would yield a trivial printability value of zero.

What follows is a set of nondimensionalized equations that enable the identification of the important dimensionless groups that need to be tuned toward efficient printability.

A thin filament approximation is used, and by focusing on a small part of the melt electrospun stable jet region, a one-dimensional momentum balance is made by considering the various forces affecting the jet profile. The jet is subjected to: (a) Coulombic electrostatic, viscous, elastic, surface tension, and gravitational forces. Assuming axisymmetry along the path from the tip of the spinneret up to the surface of the collector (at distance, d) and using the characteristic quantities defined in Table 3, the dynamics of the melt electrospun jet can be modeled using the following system of nondimensional equations, where R is the jet radius divided by the characteristic jet radius $R_o$ just outside of the needle tip, v is the jet velocity divided by the characteristic velocity $v_o$, R is the jet radius, and the prime indicates derivatives with respect to the spinline coordinate z:

A(1) Conservation of Mass—Continuity:

$$R^2v=1$$

A(2) Conservation of Momentum:

$$Revv' = Bo + 3(1-r_n)\frac{(R^2v')'}{R^2} + \frac{T_p'}{R^2} + Ca\frac{R'}{R^2} + E_p\left(\sigma\sigma' + \beta EE' + \frac{2E\sigma}{R}\right)$$

where Re, Bo, Ca, and $E_p$ are defined in Table 3.

A(3) Conservation of Charge:

$$\sigma=R$$

A(4) Electric Field:

$$E_t = \frac{1}{(1+2z-z^2/\chi)\sqrt{1+(R')^2}}$$

The viscoelastic nature of the polymer melt is taken into consideration by the use of the Giesekus model, which expresses the viscous polymer stress $\tau_p$ in terms of the applied deformation, which is represented by the strain rate tensor $\dot{\gamma}$ $$\tau_p + \lambda\tau_{p(1)} - \alpha\frac{\lambda}{n_p}\{\tau_p \cdot \tau_p\} = -n_p\dot{\gamma} \qquad \text{A(5)}$$

The viscous polymer stress $\tau_p$ denotes the elastic nature of the material due to normal stresses that arise during its deformation, and the strain rate tensor $\dot{\gamma}$ is given by the sum of the velocity gradient and its reciprocal. The input parameters of the Giesekus model that are determined by fitting the experimental raw data on the basis of the corresponding rheological material functions for each type of tested viscometric flow are the following: $n_p$ represents the polymer viscosity parameter, λ the relaxation time, and α the mobility factor, which is a parameter related to the anisotropic Brownian motion and/or hydrodynamic drag on the constituent polymer molecules.

The nondimensional components of the viscous polymer stress tensor $\tau_p$ are given based on the constitutive Giesekus model (Eq. (1)) in axisymmetric cylindrical coordinates as $$\tau_{p,rr} + De(v\tau_{p,rr}' + v'\tau_{p,rr}) + \alpha\frac{De}{r_n}\tau_{p,rr}^2 = -r_nv' \qquad \text{A(6)}$$

$$\tau_{p,zz} + De(v\tau_{p,zz}' - 2v'\tau_{p,zz}) + \alpha\frac{De}{r_n}\tau_{p,zz}^2 = -2r_nv' \qquad \text{A(7)}$$

These dimensionless numbers calculated using the above equations are further summarized in Table 3 below.

TABLE 3

Characteristic quantities along with nondimensional numbers obtained based on the governing equations

| | | |
|---|---|---|
| **Characteristic quantities** | | |
| Length | $R_o$ | |
| Velocity | $v_o = \frac{Q}{\pi R_o^2}$ | |
| Electric Field | $E_o = E(0) = \frac{2V_p}{R_o \ln(1 + 4d/R_o)}$ | |
| **Dimensionless groups and their definitions** | | |
| Bond number | $Bo = \frac{\rho g R_o^2}{\eta_o(T_m)v_o}$ | $\left(\frac{\text{gravity}}{\text{inertia}}\right)$ |
| Electrostatic force parameter | $E_p = \frac{\varepsilon_o E_o^2 R_o}{\eta_o(T_m)v_o}$ | $\left(\frac{\text{electrostatic}}{\text{inertia}}\right)$ |
| Capillary number | $Ca = \frac{\eta_o(T_m)v_o}{\gamma}$ | $\left(\frac{\text{inertia}}{\text{surface tension}}\right)$ |
| Reynolds number | $Re = \frac{\rho v_o R_o}{\eta_o(T_m)}$ | $\left(\frac{\text{inertia}}{\text{viscous}}\right)$ |
| Deborah number | $De = \frac{\lambda v_o}{R_o}$ | $\left(\frac{\text{relaxation time}}{\text{time scale of flow}}\right)$ |

Initiation of the printing process requires: (a) droplet emergence, (b) successful Taylor cone formation, and (c) subsequent emergence of a charged jet, which is electrostatically drawn across the spinline coordinate in the free-flow regime. All phenomena are dependent on the relative importance of the forces applied at the polymer melt jet.

Downstream pulling forces such as the gravitational and the electrostatic Coulombic forces are related to the Bond (Bo) number and the electrostatic force parameter ($E_p$), respectively. Upstream resistive forces such as the viscous, the elastic, and the surface tension forces are related to the Reynolds (Re) number, the Deborah (De) number, and the Capillary (Ca) number. According to the electrospinning operating principle, Taylor cone formation occurs when the electrostatic forces overcome the capillary forces. Jet initiation and the electrostatic drawing of the polymer melt jet are strongly dependent on the viscoelasticity of the polymer melt. If the gravitational forces, along with the electrostatic drawing forces caused by the accumulation of the charges at the jet-ambient air interface, overcome the viscous and elastic stresses that are applied to the polymer melt, jet initiation occurs. Thus, the proposed Printability Number should assume values within a domain defined by a set of independent material, process, and geometry-related parameters for which the printing process can be realized.

A new dimensional analysis is employed based on measurable polymer properties and controllable process parameters. Consistent with standard engineering practice, simplified dimensionless numbers are derived by taking the product of the formulated ones. Specifically, seven dimensionless groups are formulated ($\Pi_{1,2\ \ldots\ 7}$) based on the procedure detailed above. To this end, the $N_1$ number given by Eq. (9) is defined as the Printability Number for a stationary collector and denoted as $N_{PR,1}$ $$N_{PR,1} = \frac{\gamma^{1/2}\varepsilon^{1/2}}{g^{1/2}\lambda\rho}\frac{T_t}{T_C}\frac{R_o}{d}\frac{V_p}{Q\eta_p(T_m)} \quad (12)$$

where $\eta_p(T_m)$ denotes the melting temperature dependency of the polymer viscosity, and the characteristic jet radius just outside the needle tip, $R_o$, is assumed to be equal to the needle tip diameter.

Material functions of the Giesekus model are used for nonlinear fitting of the experimental data and the determination of model-specific input parameters for the polymer melt to be processed. As shown, the values of the loss modulus, G", i.e., the energy dissipated as heat, are higher than the values of the storage modulus, G', i.e., the energy stored as elastic energy, over a broad range of frequencies for the PCL that was used during MEW processing. In the linear viscoelastic region, i.e., relatively small strains and strain rates as would be encountered at the relatively low flow rate conditions of the melt electrospinning writing process (<50 μL/h), the shear viscosity of the polymer melt can be considered to be Newtonian (i.e., the zero-shear viscosity, $\eta_o(T_m)$). Up to a shear rate of 10 $s^{-1}$ the shear viscosity of PCL is constant. In the linear viscoelastic region, the uniaxial extensional viscosity of the melt, i.e., the Trouton viscosity, is equal to three times the Newtonian (zero-shear) viscosity, $\eta_o(T_m)$ $$\eta_p(T_m)=3_o(T_m) \quad (13)$$

Substituting the Trouton viscosity into Eq. (12) yields the following Printability Number, $N_{PR,1}$:

$$N_{PR,1} = \frac{1}{3}\frac{\gamma^{1/2}\varepsilon^{1/2}}{g^{1/2}\lambda\rho}\frac{T_t}{T_C}\frac{R_o}{d}\frac{V_p}{Q\eta_o(T_m)} \quad (14)$$

The zero-shear viscosities obtained from the rheological data for three different melting temperatures ($T_m$=70, 80, and 90° C.) are fitted using an Arrhenius type equation in order to obtain the activation energy of flow ($\Delta H/R_{ig}$) (SI:K)

$$\eta_o(T_m) = \eta_o(T_{ref})\exp\left[\frac{\Delta H}{R_{ig}}\left(\frac{1}{T_m} - \frac{1}{T_{ref}}\right)\right] \quad (15)$$

where ΔH is the activation energy (SI: J/mol), $R_{ig}$ is the universal gas constant (SI: J/K mol), and $T_{ref}$ is the reference temperature. Substituting Eq. (15) into Eq. (14) yields the following definition of the Printability Number, $N_{PR,1}$:

$$N_{PR,1} = \frac{1}{3}\frac{\gamma^{1/2}\varepsilon^{1/2}}{g^{1/2}\lambda\rho}\frac{T_t}{T_C}\frac{R_o}{d}\frac{V_p}{Q\eta_o(T_{ref})\exp\left[\frac{\Delta H}{R_{ig}}\left(\frac{1}{T_m} - \frac{1}{T_{ref}}\right)\right]} \quad (16)$$

TABLE 4

Material properties of PCL used

| Parameters | Values |
|---|---|
| Zero shear rate viscosity (at 78° C.) ($\eta_o$) | 3203 Pa · s |
| Relaxation time (λ) | 0.08 s |
| Activation energy of flow ($\Delta H/R_{ig}$) | 4407.8K |
| Density of PCL (at 25° C.) | 1145 $kg/m^3$ |
| Surface tension coefficient (γ) | 30 mN/m |
| Relative permittivity ($\varepsilon_r = \varepsilon/\varepsilon_o$) | 3.1 |

$N_{PR,1}$ can be computed using Eq. (16) for the melting range of PCL (70° C.≤$T_m$≤90° C.) and a prescribed set of typical process and material parameters. The values of the material parameters (summarized in Table 4) are either derived from literature or through fitting of the rheological data of the PCL used in processing for scaffold fabrication. In order to assure that NPR assumes values within a valid domain, each range is determined based on previously reported studies where PCL has been successfully processed by way of MEW. Validation of the previously reported ranges is performed through preliminary experiments with the present MEW system. Thus, a range of volumetric flow rates (25 μL/h≤Q≤50 μL/h) is applied for a 21 gauge needle tip diameter ($D_t$=2·$R_o$), for collector distances (d) of 10 mm to 30 mm and a range of applied voltage potentials (10 kV≤$V_p$≤15 kV).

The normalized $N_{PR,1}$ is obtained by dividing the computed $N_{PR,1}$ value with the $N_{PR,1}$ value that defines the lower end of the printability window bounded by the material's melting range for $T_{ref}$=70° C. and $Q_{max}$=50 μL/h. The temperature of the polymer melt inside the reservoir ($T_o$) is normalized with respect to the reference temperature ($T_{ref}$=70° C.), i.e., $T^*=T_o/T_{ref}$, $T^*=T_m/T_{ref}$ since $T_o$ assumes the melt temperature value ($T_m$). The printability window is seen to depend significantly on the volumetric flow rate, with the smaller Q (25 μL/h) yielding significantly larger $N^*_{PR,1}$ values compared to that obtained at the larger Q (50 μL/h). This trend is consistent with recent phenomenological observations that reflect stable printing by way of MEW under low volumetric flow rates. As T* increases within each printability window, $N^*_{PR,1}$ increases exponentially due to the Arrhenius temperature dependence of the polymer melt viscosity, implying that for higher melt temperature conditions, the material can be electrospun more efficiently. This relationship indicates that for prescribed $D_t$, Q, and $V_p$ settings, melt temperature conditions approaching the higher end of the material's melting temperature range (90° C. for PCL) enable earlier droplet emergence compared to the melt temperature conditions that approach the lower end of the material's melting temperature range, due to an increased volumetric flow rate inside the needle tip.

The $N_{PR,1}$ formulation (Eq. (16)) implies that the electrical field strength ($V_p$/d) and the volumetric flow rate (Q) are the key independent parameters toward efficient printability (fiber mesh printing with consistent dimensional characteristics) provided that the melting and ambient conditions in the polymer melt supply regime and the temperature profile along the spinline in the free-flow regime are not significantly perturbed during each printing event. $N_{PR,1}$ scales as $N_{PR,1}$~1/Q and $N_{PR,1}$~$V_p$/d. This validates the physical significance of the derived number that expresses the key combinatorial role of electrostatic, viscous, and inertial forces toward steady electrospinning conditions as previously demonstrated for solution-based electrospinning systems. Furthermore, all of the dimensionless groups are a function of Q-dependent inertial terms (see Table 3). Thus, the functional relationship between $N_{PR,1}$ and each dimensionless number is computed for the prescribed Q range and three different $V_p$ values spanning the $V_p$ range. The results are plotted for $N^*_{PR,1}$ as a function of the Re, Ca, De, and $E_p$ numbers revealing that upon prescribing the melting conditions, a unique printability window can be defined for each $V_p$ setting.

The printability window defined by the $V_p$ range and the Q range remains to be optimized with respect to efficient printability through in situ process monitoring and morphological characterization of the printed meshes as described below via the experimentally collected data.

During the experimental procedure, the temperature at the surface of the glass syringe ($T_s$) is set to 78° C. The values for the remaining independent process parameters used for the $N_{PR,1}$ computation are set to the following for the initiation of the melt electrospinning process: (a) Q is equal to 50 μL/h, (b) $V_p$ is equal to 12.5 kV, and (c) d is equal to 20 mm.

To enable real-time monitoring of the process in the free-flow regime, a universal serial bus microscope camera is mounted on the open side of the enclosure box and focused on the needle tip. For this procedure, the prescribed experimental conditions reside within the printability window corresponding to a $N^*_{PR,1}$ equal to 1.34. The observation of the process during its early stages contributes to an understanding of the dynamics and the underlying physical mechanisms governing the process, as described below.

Initially, the polymer melt enters the free-flow regime owing to the electrostatic volume forces developed from the applied voltage potential at the tip and the mechanical force applied by the syringe pump (proportional to the pressure drop of the melt through the needle). After approximately 12 min, the jet is observed to exhibit an elongated shape, indicating that the downstream electrostatic forces along with the gravitational forces are sufficiently large to overcome the upstream resistive forces (viscous, elastic, and surface tension forces). At the point where the downstream forces overcome the upstream resistive forces, the formation of the Taylor cone is observed within approximately an additional 3 min. Immediately following the formation of the Taylor cone, a jet emerges and is electrostatically drawn between the needle tip and the collector.

By extending the time course for process monitoring in the free-flow regime, it is observed that for the initially prescribed combination of process parameters, excess material is generated due to the imbalance between the downstream pulling and upstream resistive forces. Such excess material that is not fully stretched periodically disturbs (every 5 min) the flow field in the spinline regime. After the excess material enters the free-flow regime, the cone shape is initially transformed into an oblique shape, and the partially stretched melt driven by the downstream forces leads to the relocation of the Taylor cone, i.e., the cone is pushed away from the tip of the needle, and a cylindrical body of melt occupies the distance between the tip of the needle and the Taylor cone. To achieve steady-state conditions, i.e., steady-state formation of the Taylor cone at the tip of the needle and the emerging polymer melt jet, the critical process parameters, $V_p$ and Q, need to be optimized. Such optimization specifies the relevant Printability Number $N_{PR,1}$ at which efficient printability is achieved. This optimization step thus aims to eliminate the perturbations observed under nonequilibrium processing conditions. Upon optimization, an equilibrium state, i.e., state at which the downstream pulling and upstream resistive forces are balanced, is achieved.

The tuning of the critical independent parameters in order to achieve equilibrium conditions is carried out in a stepwise manner. As a first step, the collector is moved closer to the needle tip (d=15 mm) to increase the electrical field strength. When the tip to collector distance d≤10 mm, arching occurs due to excess ionized air molecules and dry ambient conditions (humidity<25%). At such relatively small distances (d), the arching phenomenon becomes more pronounced for applied voltages that are ≥15 kV. By reducing the distance (d), a higher electrical field intensity facilitates stretching of the excess material collected at the tip. However, solely reducing the distance (d) is not sufficient to eliminate the periodic perturbations. To eliminate the perturbations and achieve equilibrium conditions, a reduction in the volumetric flow rate (Q) is also required. This is suggested by the relative importance of the Q-dependent inertial forces with respect to the $V_p$-dependent electrostatic forces, as guided by the $N_{PR,1}$ formulation denoted in Eq. (16). The decrease of the volumetric flow rate to Q=25 μL/h results in the formation of a Taylor cone directly below the needle tip. However, chaotic jet movement occurs close to the collector plate, and stable jet cannot be achieved. In order to eliminate the instabilities and establish equilibrium state conditions, the applied voltage potential can be decreased to 11.5 kV, yielding stable cone-jet formation for a period of 30 min after which the printing process could start.

The observation that the optimized Printability Number $N^*_{PR,1}$=2.55) is smaller than the non-optimized Printability Number $N^*_{PR,1}$=2.78) raises the question of self-consistency of the proposed Printability Number. This finite difference in magnitude is attributed to a phenomenon that has previously been observed in electrohydrodynamic (EHD) cone-jets with highly viscous conductive polymer solutions. Using voltage-flow rate ($V_p$–Q) operating diagrams, it has been shown that for a single Q value, steady cone-jets can be achieved for $V_p$ values lying within a range of 1 kV. Similarly, in the present example, Q is maintained at 25 μL/h, and the voltage is decreased from 12.5 kV to 11.5 kV. The decrement in $V_p$ is aimed at eliminating the chaotic jet movement close to the collector plate that is likely caused by repulsive forces between the in-flight fiber and previously charged deposited material on the collector rather than periodic flow disturbances that are preliminarily eliminated. Therefore, the small difference between the $N^*_{PR,1}$ values does not affect the self-consistent scale of the Printability Number since it is related to the process physics, as previous work has demonstrated. Thus, by tuning the $N^*_{PR,1}$ number from an initial value of 1.34 to 2.55, the observed perturbations that may affect the downstream structural formability of the printed meshes and preclude efficient printability can be eliminated. This is validated hereafter by reproducibly printing layered meshes of woven and nonwoven topographies at both the optimum and non-optimum printability settings.

After steady equilibrium conditions are achieved (i.e., for the optimized $N^*_{PR,1}$), the "square-wave" experiment can be conducted using the translational stage speed as the main variable. The goals are: (a) to observe the different fiber patterns and diameters that can be produced over a wide range of translational stage speeds and (b) to determine the critical stage speed ($U_{CR}$), at which aligned fibers can be deposited on the translating collector. At lower speeds (2-8 mm/s), random fiber deposition yields nonwoven structures typified by overlapping fibers with multiple fusion points. At intermediate translation speeds (8-83 mm/s), repeatable coiling structures, for which the frequency of the overlap monotonically decreases as the stage speed increases, are realized. When the translational stage speed reaches 83 mm/s a well-aligned fiber with average diameter, $D_f$=23±1.5 μm (micrometer) could be printed on the collector. It should be noted that the changes in the translational stage speed affect the drawdown of the fiber, and thus the changes in the resulting pulling force have the potential to disturb the equilibrium condition, especially at $U_T \gg U_{CR}$. Thus, the optimization of the translational stage speed needs to be carried out in conjunction with the optimization of $N^*_{PR,1}$. To this end, $U_T$ is incorporated as an additional independent parameter in the dimensional analysis, and the derived $N_2$ term (Eq. (11)) is used as the Printability Number when the collector is moving. The modified Printability Number is denoted as $N_{PR,2}$, and its final form is obtained by multiplying the $N_{PR,1}$ with the $\Pi_8$ term.

$$N_{PR,2} = \frac{1}{3}\frac{\gamma^{1/2}\varepsilon^{1/2}R_o^{1/2}}{g\lambda\rho d}\frac{T_t}{T_C}\frac{V_p U_T}{Q_o(T_{ref})\exp\left[\frac{\Delta H}{R_{ig}}\left(\frac{1}{T_m}-\frac{1}{T_{ref}}\right)\right]} \tag{17}$$

A normalized Printability Number, $N^*_{PR,2}$, is obtained by dividing the computed $N_{PR,2}$ value (based on Eq. (17)) with the $N_{PR,1}$ value (based on Eq. (16)) that defines the lower end of the printability window bounded by the material's melting range for $T_{ref}$=70° C. and $Q_{max}$=50 μL/h. The normalized Printability Number $N^*_{PR,2}$ is computed for each fiber pattern where optimum printability is achieved when $U_T$ is tuned to its critical value ($U_T = U_{CR}$).

Figure 14:
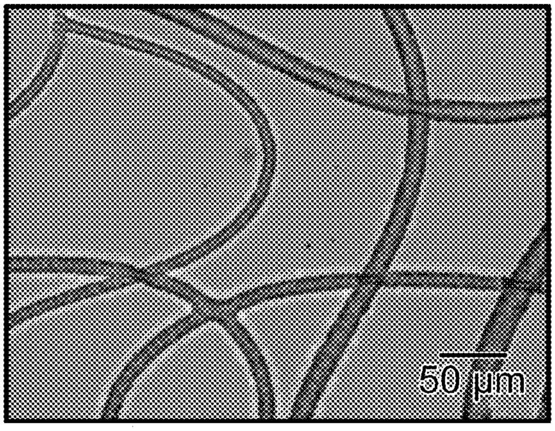
FIGS. 14-18 are a set of reproductions of photographic images showing scaffolds fabricated from poly(caprolactone) ("PCL") melts by a method according to an embodiment of the present invention, the scaffolds having different configurations according to other embodiments of the present invention and the scaffolds of FIGS. 16, 17 and 18 specifically being woven scaffolds.
Figure 15:
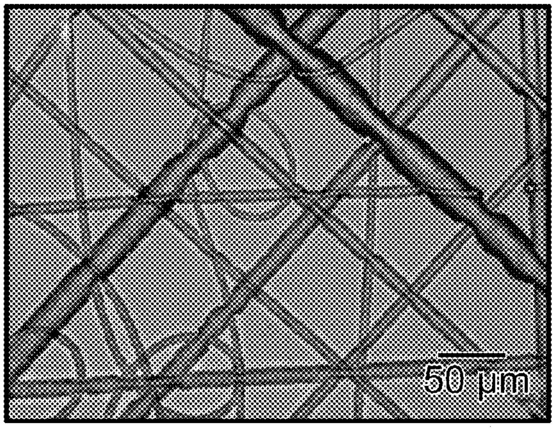
Figure 16:
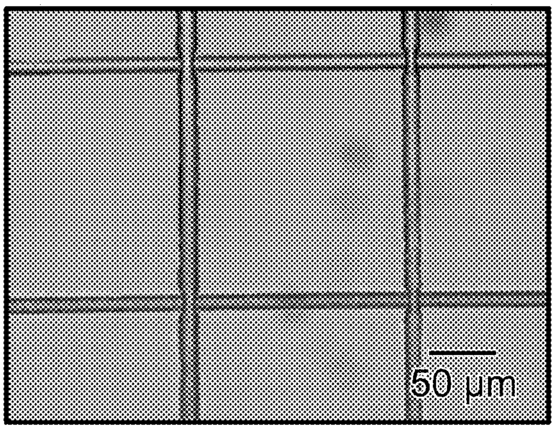
Figure 17:
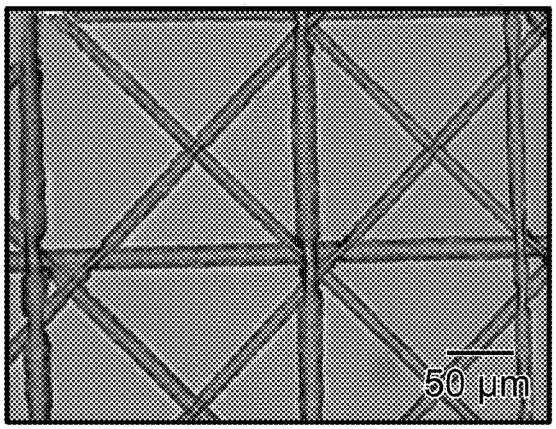
Figure 18:
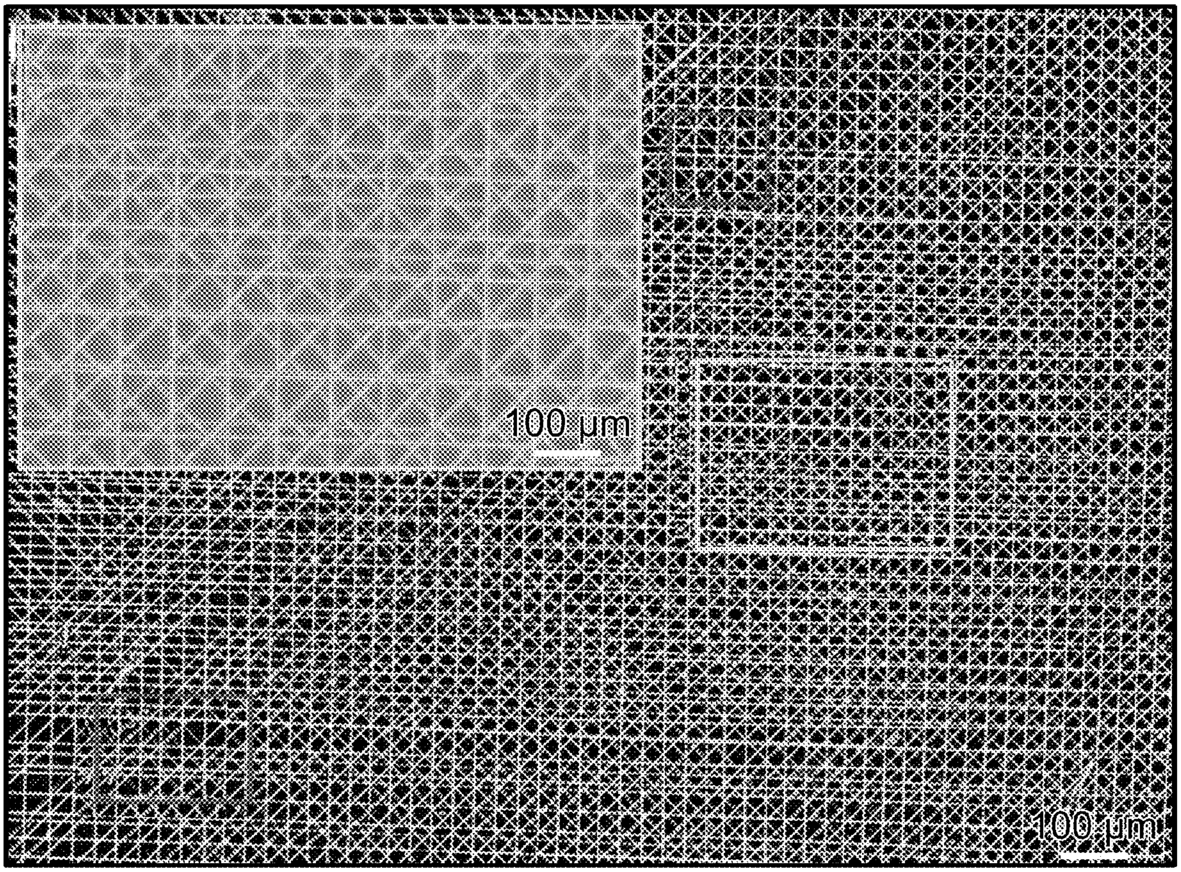

With the setup and calculations above, interwoven fiber meshes can be made for use as biological scaffolds. Layered meshes with woven and nonwoven architectures are fabricated using various $N^*_{PR,2}$ settings. Woven meshes with "0-90 deg" and "0-45-135-90 deg" pore architectures are fabricated using optimized and non-optimized $N^*_{PR,2}$ settings. When $N^*_{PR,2}$ is not optimized, irregular structures are observed. This is shown in FIG. 14, which is obtained at an $N^*_{PR,2}$=31.9, where $U_T$=25 mm/s<$U_{CR}$. When $N^*_{PR,2}$ is increased to 57.63 by independently tuning the stage speed ($U_T$=85 mm/s>$U_{CR}$) while neglecting equilibrium conditions in the free-flow regime, aligned structures with variable average fiber diameters (Df=27±14 μm) are observed, as shown in FIG. 15. On the other hand, precise printing of mesh architectures composed of well-aligned fibers with uniform average diameters (Df=23 μm±3.7 μm) can be produced for an optimal Printability Number of $N^*_{PR,2}$=106. The produced fibers at this optimal printability setting are shown in FIGS. 16, 17, 18, 21 and 22 bearing the hallmarks of equilibrium state conditions in tandem with appropriate tuning of $U_T$ at its critical value.

Figure 19A:
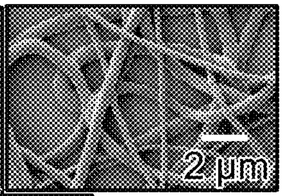
FIGS. 19-22 are a set of reproductions of photographic images, and respective enlarged sub-figures (19A, 20A, 21A and 22A), showing fibrous scaffolds fabricated from PCL melts and a method according to an embodiment of the present invention, the scaffolds of FIGS. 19 and 20 fabricated using conventional solution electrospinning technology, said scaffolds having a non-woven configuration, and the scaffolds of FIGS. 21 and 22 fabricated by a method according to an embodiment of the present invention and having a woven configuration with different porous microarchitectures.
Figure 19:
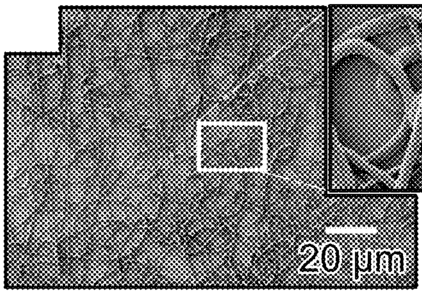
Figure 20A:
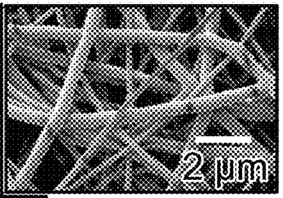
Figure 20:
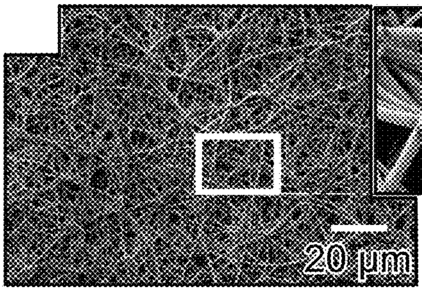
Figure 21A:
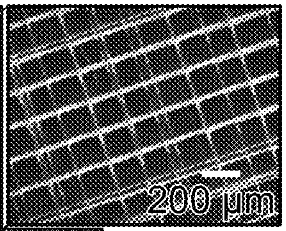
Figure 21:
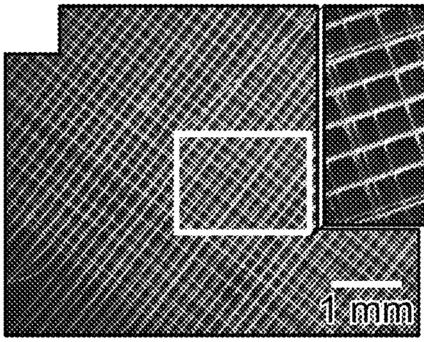
Figure 22A:
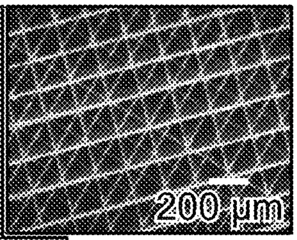
Figure 22:
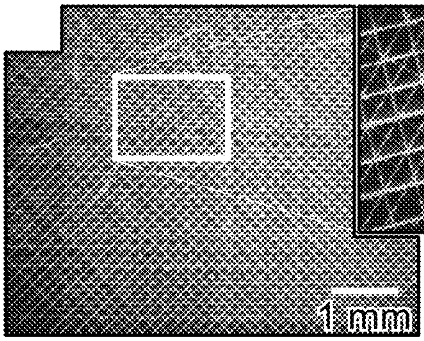

To characterize the effects of the substrate geometry on cell confinement states, in a first set of experiments, neonatal human dermal fibroblasts (NHDFs) were seeded directly on flat glass surfaces (to serve as controls) as well as on solution electrospun substrates (SES-1 min in FIG. 19 and SES-3 min in FIG. 20) and the precision-stacked microarchitectures (MEW|0-90° in FIG. 21 and MEW|0-45° in FIG. 22). The shapes of the fibroblasts were characterized at 24 h after seeding.

Figure 23:
FIG. 23 is a schematic diagram of a petri dish.
Figure 24:
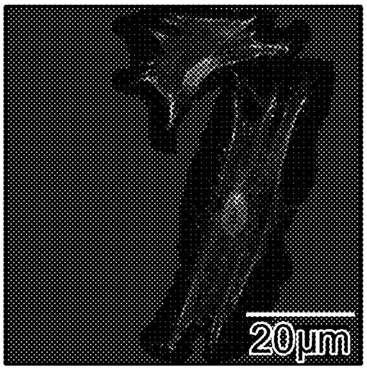
FIGS. 24 and 25 are images showing attached neonatal human dermal fibroblasts' (NHDFs) shapes on a conventional flat culture substrate with cell shape control via tailoring of the porous microarchitecture of the scaffolds according to embodiments of the present invention.
Figure 25:
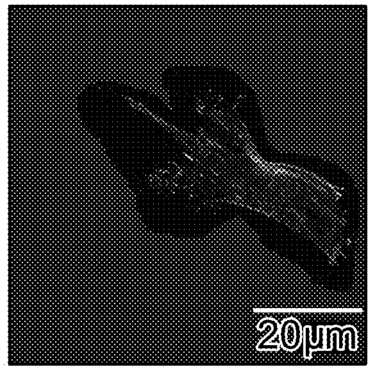

It was observed that the cells seeded directly on the flat glass surfaces develop typical fibroblast morphologies exhibiting elongated shapes and distinct actin-based motility structures (FIGS. 23-25).

Figure 26:
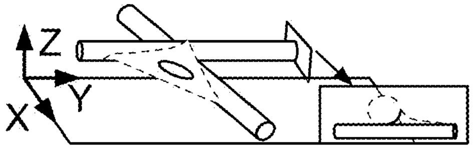
FIGS. 26-28 are schematic diagrams of cells on the MEW|0-90° scaffold with accompanying micrographs (26A, 27A, 28A and 28B), with cell shape control via tailoring of the porous microarchitecture of the scaffolds according to embodiments of the present invention.
Figure 27:
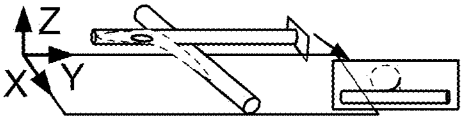
Figure 26A:
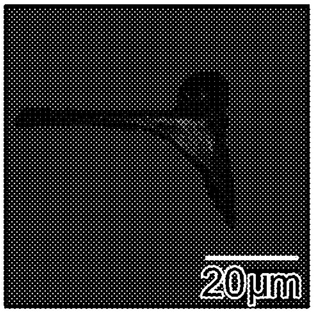
Figure 27A:
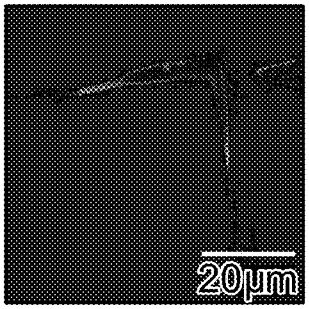
Figure 28:
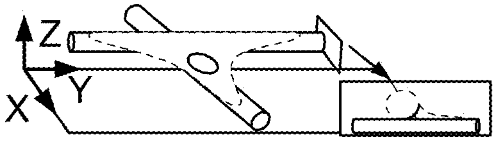
Figure 28A:
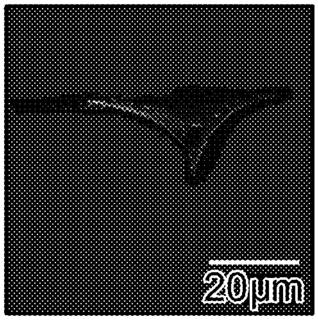
Figure 28B:
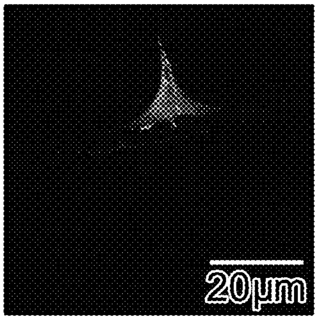

It is observed that the cells seeded on MEW|0-90° are mainly attached along single fibers and at the intersection of layered fibers. In the former case, cells adopt thin elongated shapes dictated by the curvature of the fiber, since they "grab" the exposed areas of the fiber at different planes (FIGS. 26-28). In the latter case, cells adopt uniform shapes and demonstrate spreading, the degree of which depends on the number of fibers at the intersection point.

Figure 29:
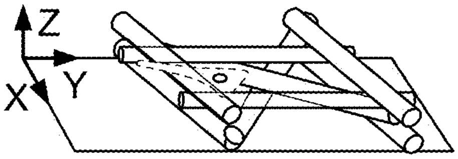
FIGS. 29 and 30 are schematic diagrams of cells on the MEW|0-45° scaffold with accompanying micrographs (29A, 29B, 30A and 30B), with cell shape control via tailoring of the porous microarchitecture of the scaffolds all according to embodiments of the present invention.
Figure 29A:
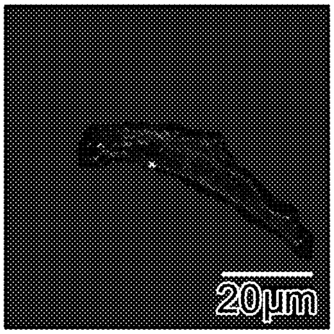
Figure 29B:
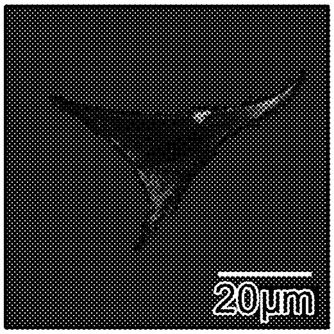
Figure 30:
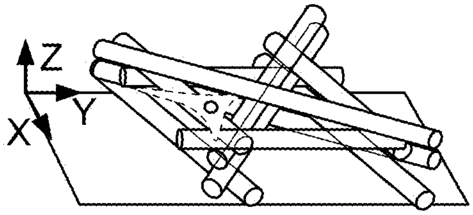
Figure 30A:
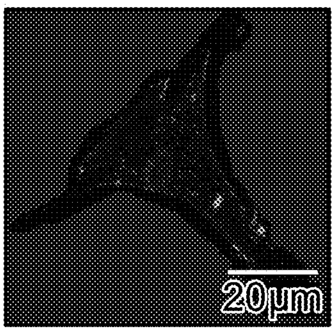
Figure 30B:
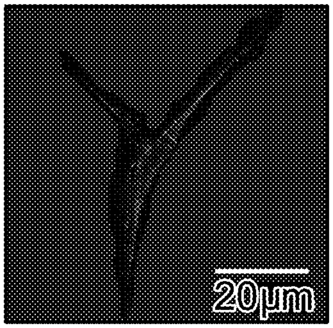
Figure 31:
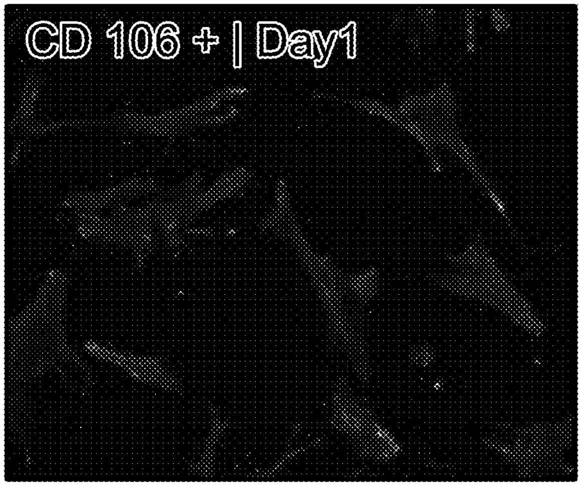
Figure 32:
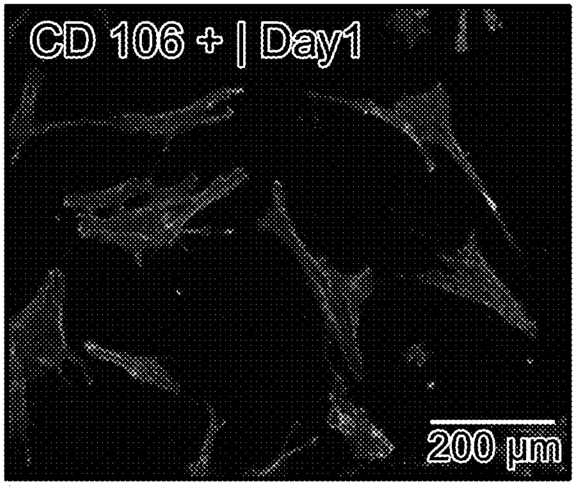
Figure 33:
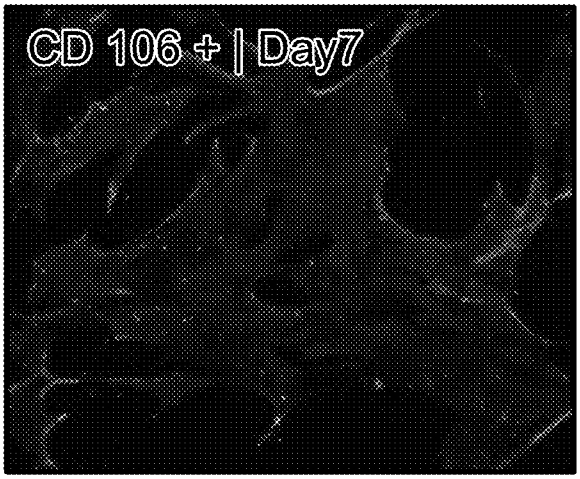
Figure 34:
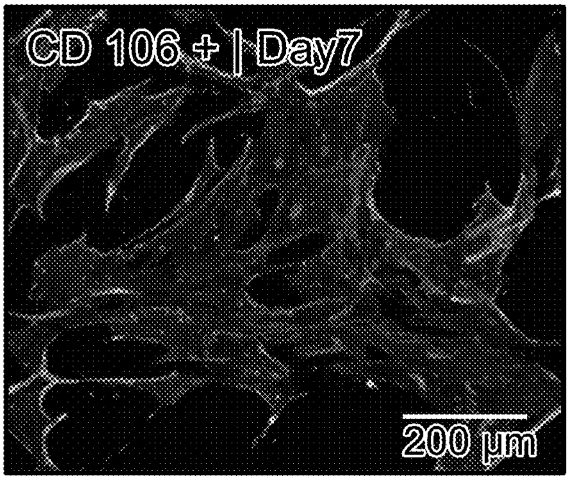
Figure 35:
Figure 36:
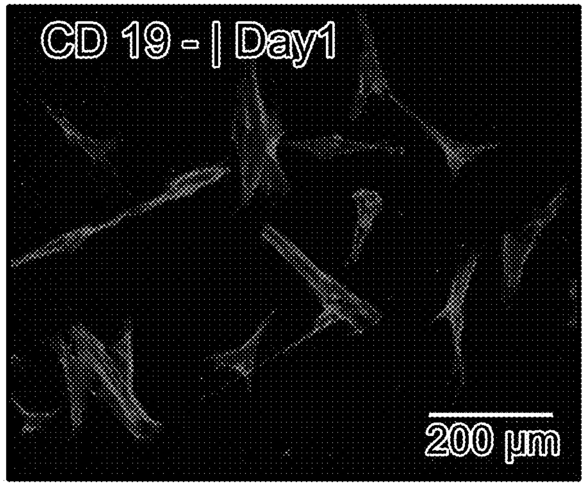
Figure 37:
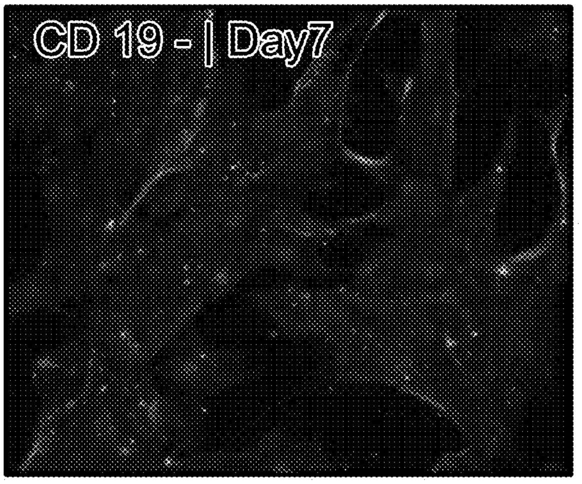
Figure 38:
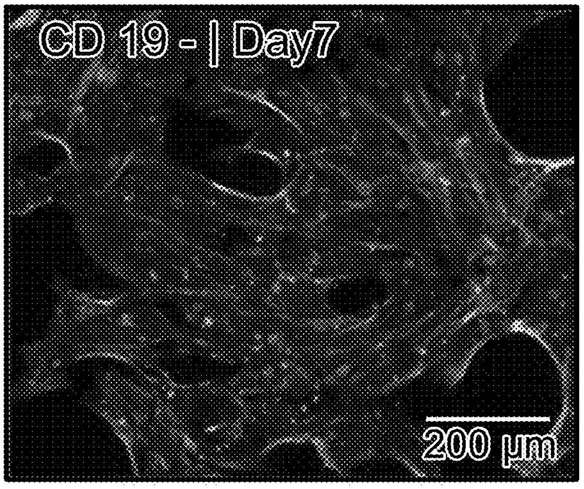
Figure 39:
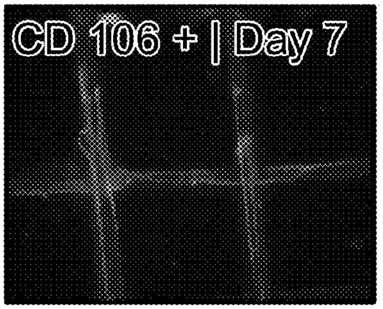
FIGS. 39-50 are multiple sets of photographic immunofluorescence images FIGS. 39, 40 and 42 showing positive marker expression and FIGS. 41 and 43 showing no negative marker expression) illustrating the expansion of stem cells on scaffolds having porous microarchitectures realized according to a method of the present invention, and the novel and unexpected finding that, under such scaffold geometries and architectures, stem cells conserve their phenotypes after 7 days of culture, which cannot be achieved with conventional substrates, the example of FIGS. 39-50 being the conservation of the stem cell phenotype for at least one week on the MEW|0-90° scaffold, whereas with the PCL flat surfaces of the embodiment of FIGS. 31-38, the phenotype of the stem cells is altered within one week, thus significantly reducing the potential for stem cell expansion.
Figure 40:
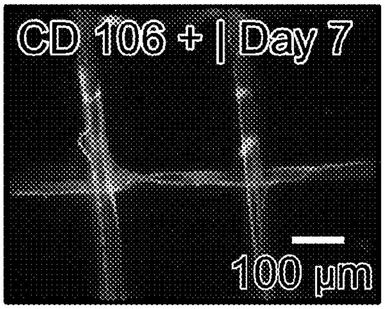
Figure 41:
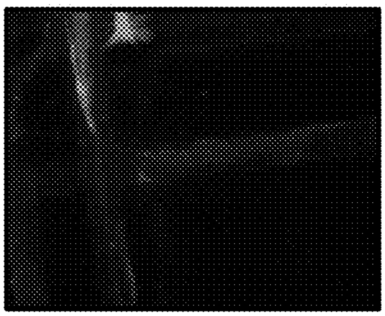
Figure 42:
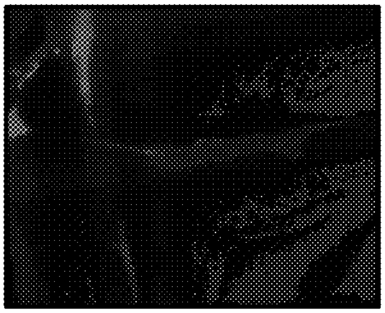
Figure 43:
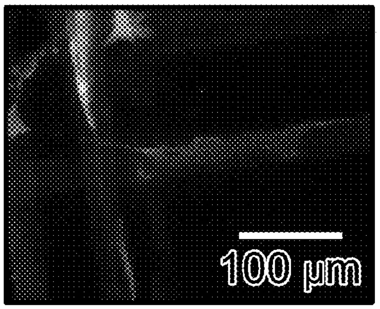
Figure 44:
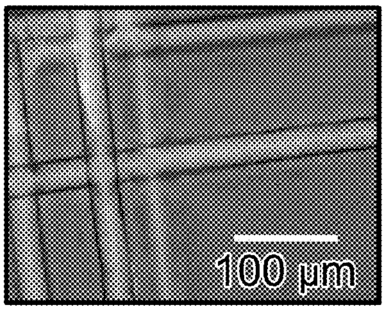
Figure 45:
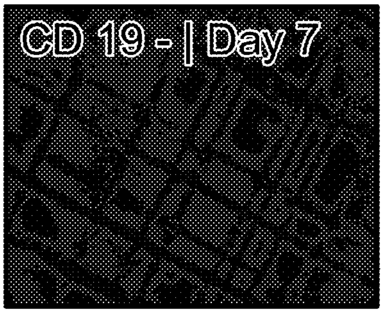
Figure 46:
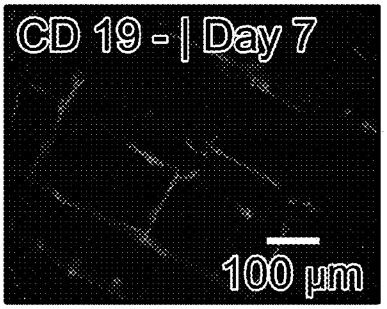
Figure 47:
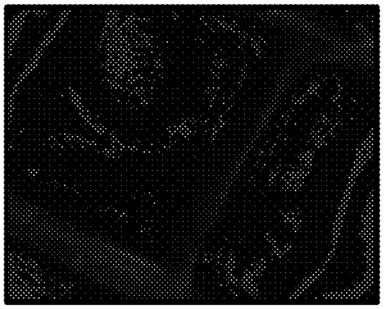
Figure 48:
Figure 49:
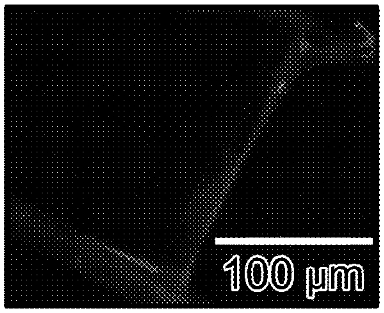
Figure 50:
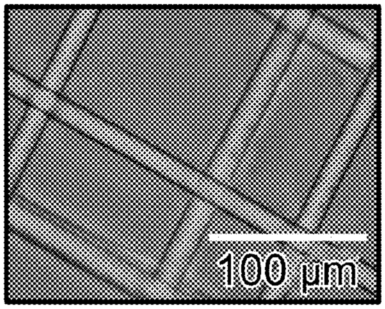
Figure 51:
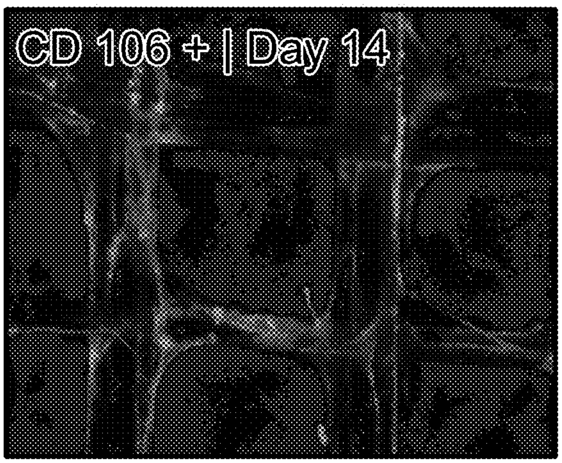
FIGS. 51-62 are multiple sets of photographic immunofluorescence images (FIGS. 51-53 showing positive marker expression and FIGS. 54 and 55 showing no negative marker expression) illustrating the expansion of stem cells on scaffolds having porous microarchitecture realized according to a method of the present invention, and the novel and unexpected finding that, under such scaffold geometries and architectures, stem cells conserve their phenotypes after 14 days of culture, which cannot be achieved with conventional substrates, the example of FIGS. 51-62 being the conservation of the stem cell phenotype for at least one week on the MEW|0-90° scaffold, whereas with the PCL flat surfaces of the embodiment of FIGS. 31-38, the phenotype of the stem cells is altered within one week, thus significantly reducing the potential for stem cell expansion.
Figure 52:
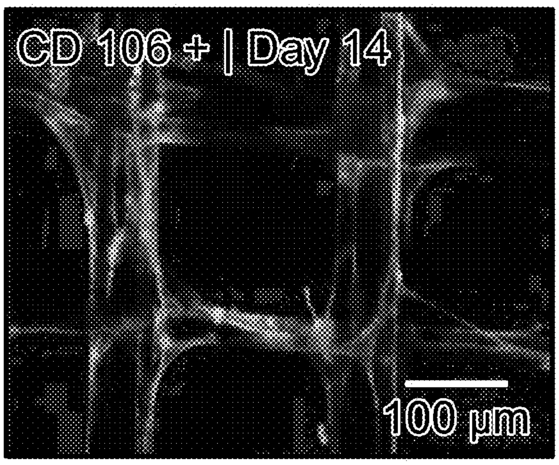
Figure 53:
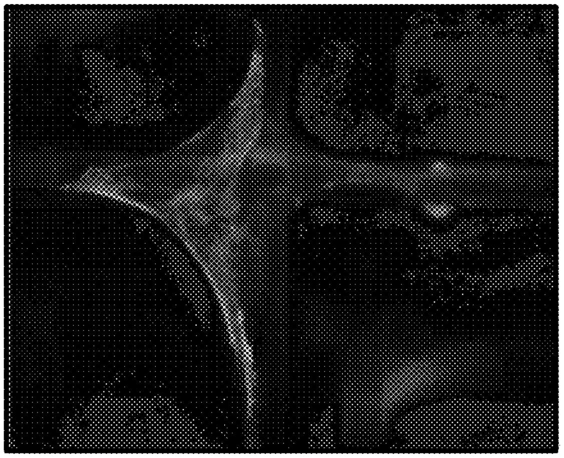
Figure 54:
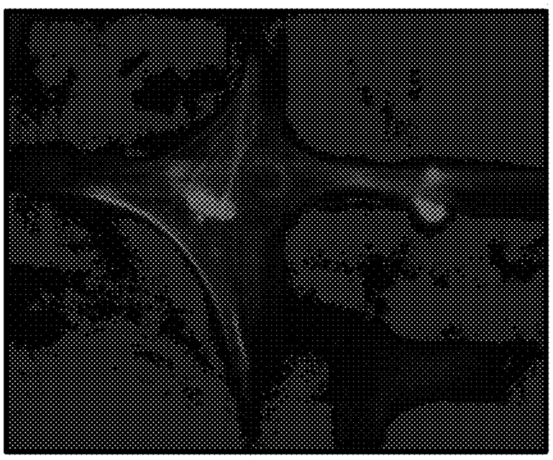
Figure 55:
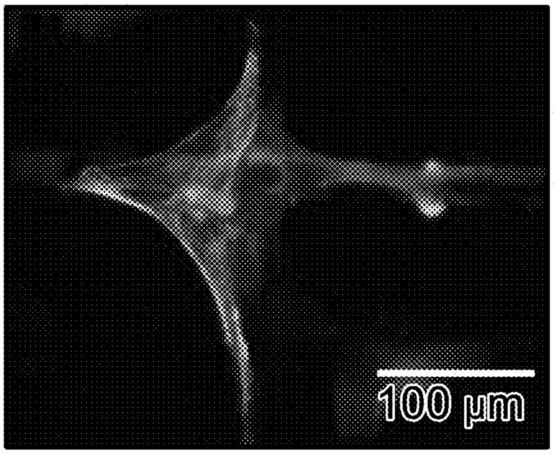
Figure 56:
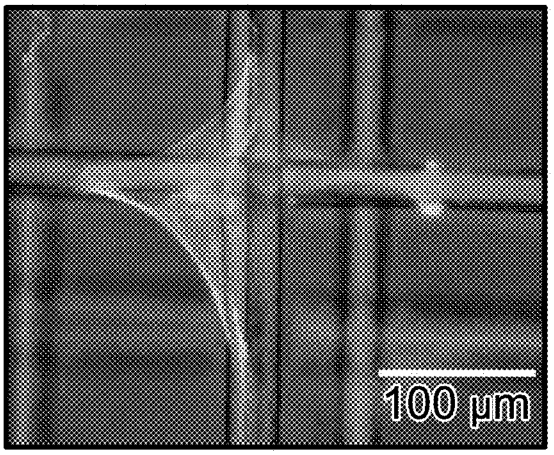
Figure 57:
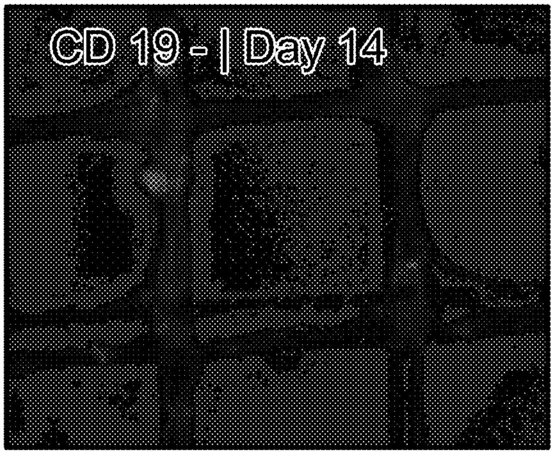
Figure 58:
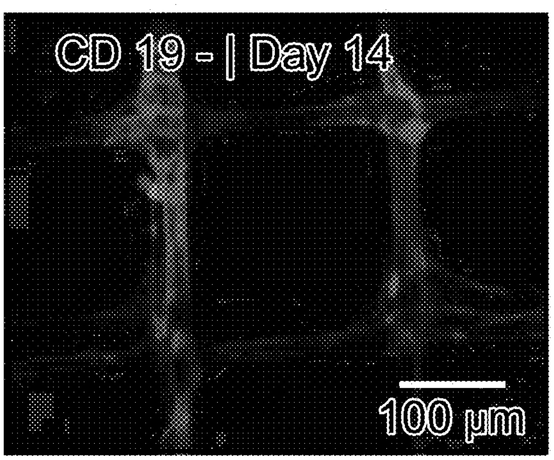
Figure 59:
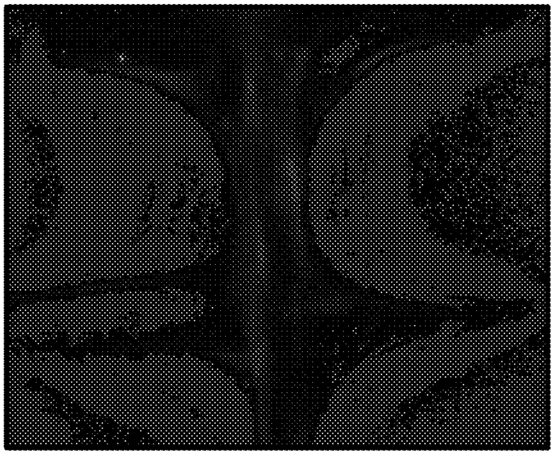
Figure 60:
Figure 61:
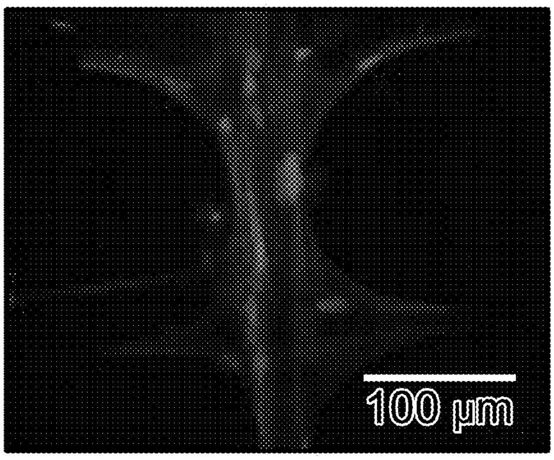
Figure 62:
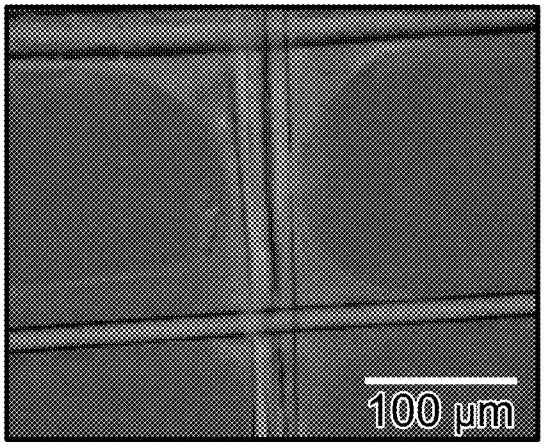
Figure 63:
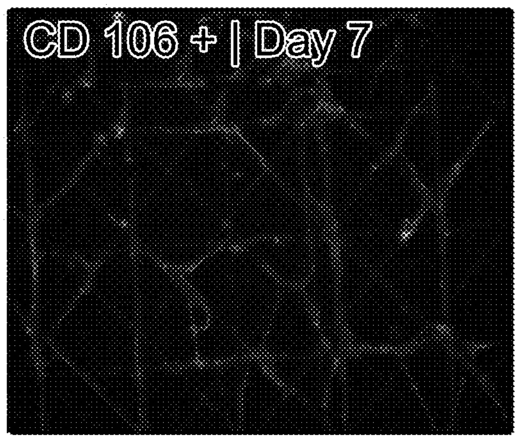
FIGS. 63-74 are multiple sets of immunofluorescence photographic images (FIGS. 63-66 showing positive marker expression and FIGS. 67-70 showing no negative marker expression) further illustrating the expansion of stem cells on scaffolds having porous microarchitectures realized according to a method of the present invention, and the novel and unexpected finding that, under such scaffold geometries and architectures (e.g., the MEW|0-45° of FIG. 22), stem cells preserve their phenotype for the first week of expansion, while the phenotype is converted in a predictable manner into a new phenotype thereafter, showing that understanding the relationships between the geometries of the scaffolds and the differentiation route of the stem cells will generate a new method that will enable the harvesting of cell populations with targeted phenotypes based on the geometry of the scaffold alone.
Figure 64:
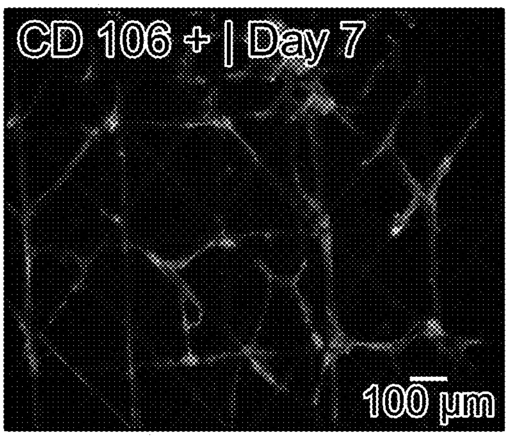
Figure 65:
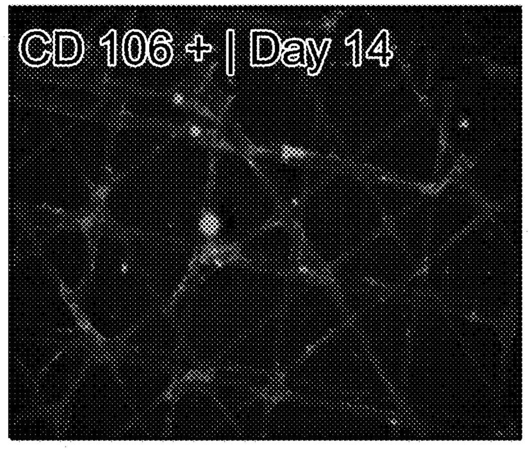
Figure 66:
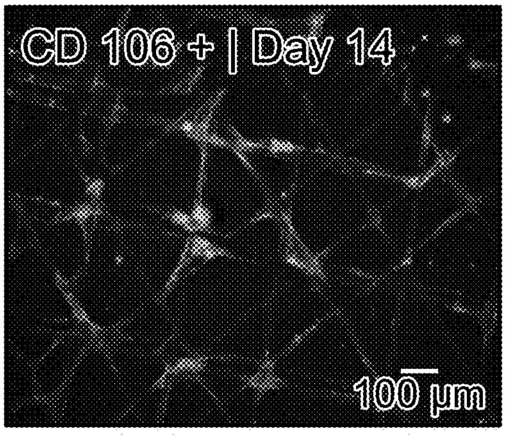
Figure 67:
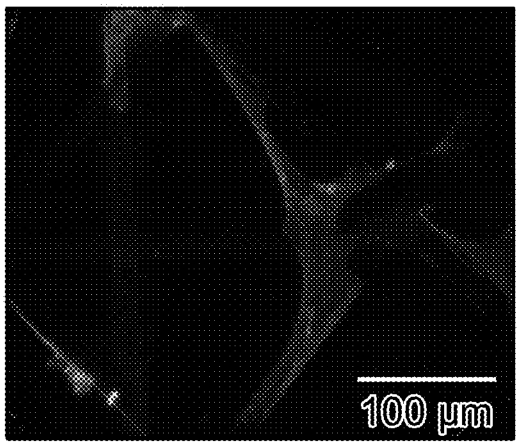
Figure 68:
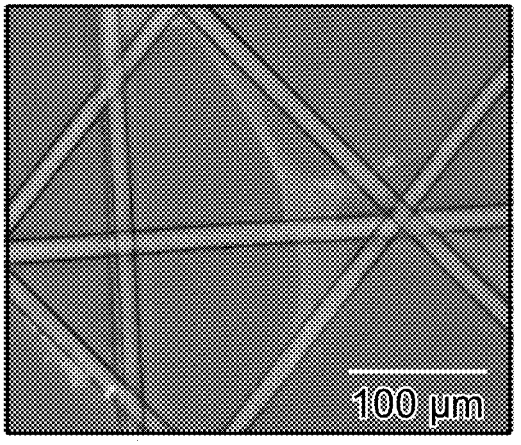
Figure 69:
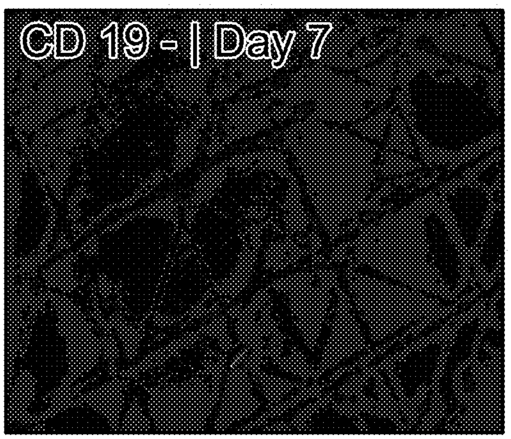
Figure 70:
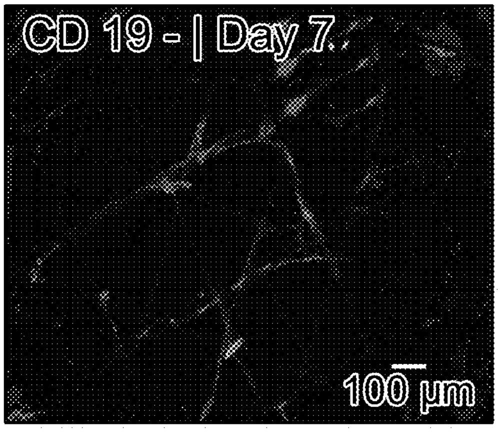
Figure 71:
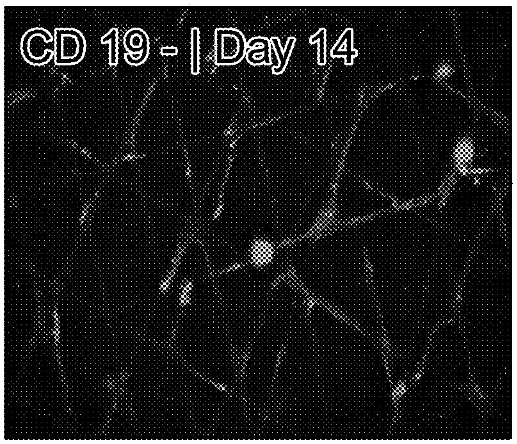
Figure 72:
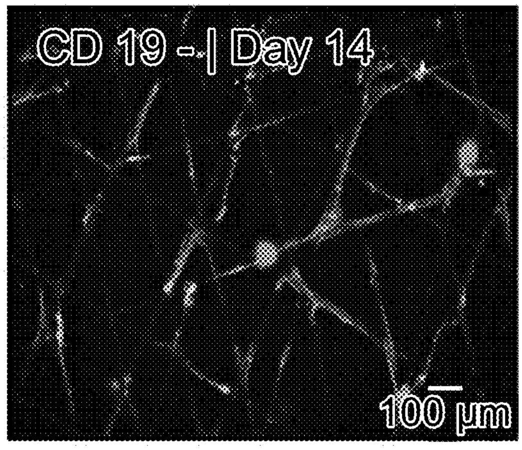
Figure 73:
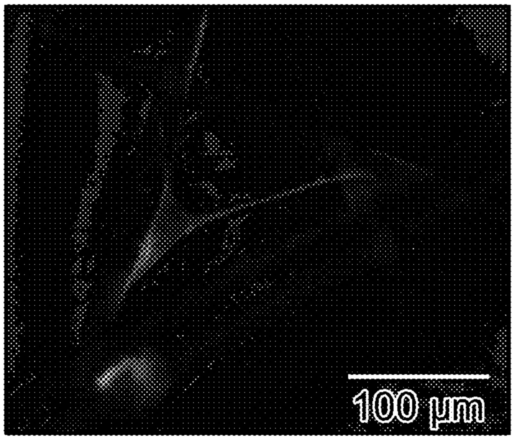
Figure 74:
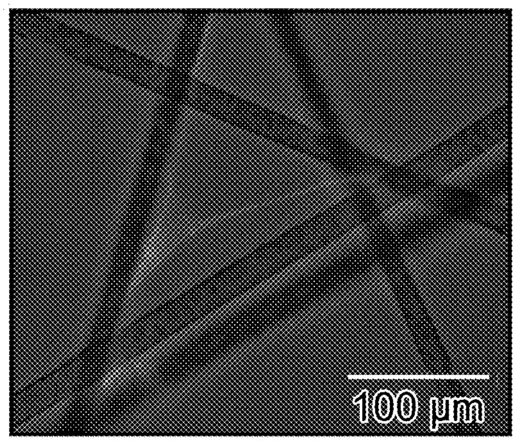
Figure 75:
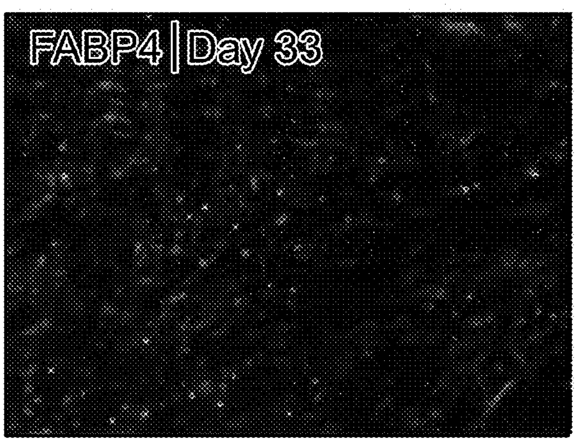
FIGS. 75-82 are multiple sets of immunofluorescence photographic images (FIGS. 75 and 76 showing positive adipocyte expression and FIGS. 77 and 78 showing bone differentiation marker expression, both 33 days after culture on conventional flat substrates, and FIGS. 79-82) showing only adipocyte differentiation marker expression on MEW scaffolds) further illustrating the expansion of stem cells on scaffolds having porous microarchitectures realized according to a method of the present invention promoting homogeneous expansion and differentiation of stem cells.
Figure 76:
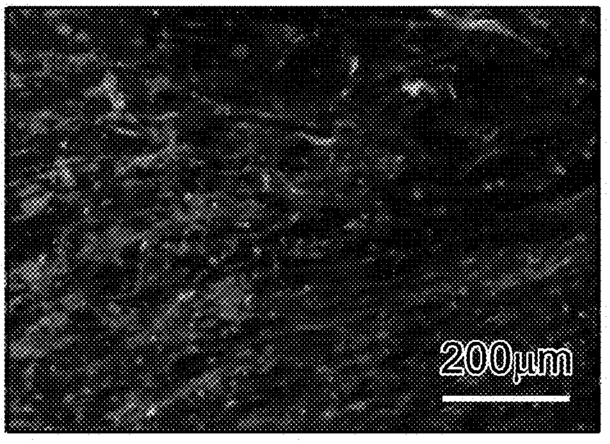
Figure 77:
Figure 78:
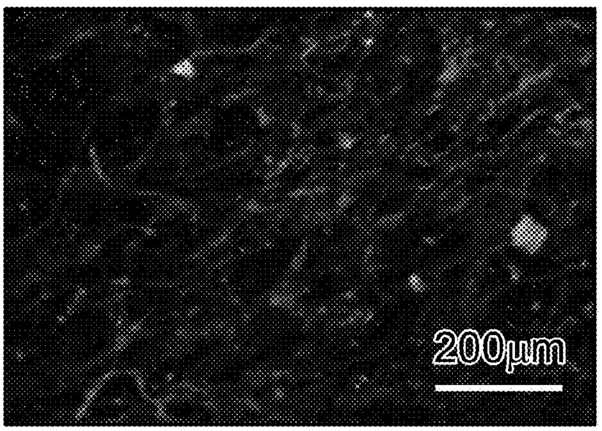
Figure 79:
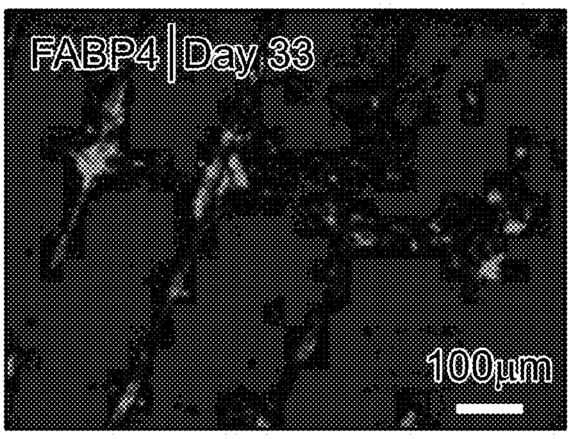
Figure 80:
Figure 81:
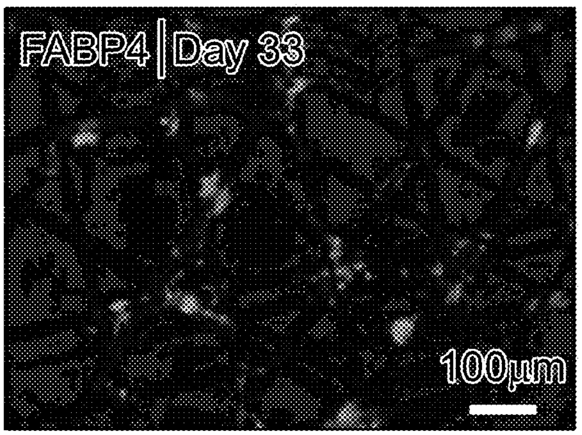
Figure 82:

Cells seeded on MEW0-45° are confined and suspended at various levels across the thickness of the substrate and within the porous microenvironments defined by layered fibers (FIGS. 29 and 30). All imaged cells develop triangular lamellar shapes consistent with the enforcing triangular microarchitecture of the substrate. The cell shapes are characterized by relative few actin stress fibers that traverse the cytoplasm and terminate in distinct filopodia, with elongated focal adhesions, FAs, sequestered to the tips of the protrusions.

Taken together, these findings qualitatively suggest that there is a tight link between the porous microarchitecture of precisely-stacked MEW fibrous substrates and the resulting cell morphologies. Different structures impose different cell confinement states. First, the cellular and subcellular morphological features of cells seeded on MEW substrates give rise to different confinement states that are different with respect to the ones observed in the unconfined cells cultured on glass coverslips. Second, there exist important qualitative differences in cell shapes and focal adhesion distributions, dependent on whether randomly-oriented solution electrospun mesh substrates or the precision-stacked woven mesh substrates fabricated via the MEW process are used.

In a second set of experiments mesenchymal stem cells, MSCs, were used. It was then hypothesized that the induced distinct confinement states, would lead to differential downstream MSCs phenotypes. Specifically, the hypothesis was that the 3-D microscale fibrous substrates would constitute a more physiological-relevant niche compared to the conventional 2-D glass substrate (controls substrate). The MSC phenotype is characterized with respect to the expression of typical positive and negative stem cell surface markers that allow for positive and negative identification that the MSCs have maintained or lost their "stemness," respectively. To experimentally verify the purity of the MSC starting cell population, MSCs are cultured on the controls substrate and tested for the complete set of the candidate positive and negative markers at Day 1 (24 hours after seeding). Indeed, it is observed that all the positive CD markers are well expressed and the negative CD markers are not expressed (FIGS. 31-36). In order to minimize the sample number that needs to be fabricated, the most and least well expressed positive and negative marker (CD106+) was chosen for the rest of the characterization studies. At Day 7, MSCs cultured on the controls express both the positive and negative marker, demonstrating that MSCs lose their "stemness" sometime within the first week of culture (FIGS. 33-38). This is in line with recent findings, according to which MSCs in standard monolayer cultures loose stem cell marker expression by Day 3 of culture.

Remarkably, it is observed that MSCs on the MEW|0-90° remain viable and self-renew by populating the effective fiber adhesive area without losing their phenotype during the first week of culture (FIGS. 39-50). The time course of the experiment was extended to two weeks, demonstrating that cells continued to proliferate without losing their stem cell marker expression (FIGS. 51-62). Then, it was tested whether an altered porous microarchitecture under a 3-D setting could result in differential MSCs phenotypes compared to the controls and the MEW|0-90° substrate at the prescribed time points. It is observed that MSCs maintain their stemness during the first week of culture on MEW|0-45° substrates (FIGS. 63-70), while they lose their MSC phenotype sometime during the second week of culture (FIGS. 65-72).

A last set of experiments was performed to study long term (after 33 days) stem cell differentiation on both flat and 3-D microscale scaffolds. The results are depicted in FIGS. 75-82, demonstrating positive adipocyte (FIGS. 75 and 76) and bone (FIGS. 77-78) differentiation marker expression 33 days after culture on conventional flat substrates and demonstrating in FIGS. 79 and 80 and FIGS. 81-82 only adipocyte differentiation marker expression on MEW scaffolds, further illustrating the expansion of stem cells on scaffolds having porous microarchitecture realized according to a method of the present invention promotes homogeneous expansion and differentiation of stem cells.

Thus, it was determined that stem cells seeded on exemplary scaffolds fabricated by the TCK method behave in a very different manner from stem cells seeded on conventional 2-D surfaces with regard to the spatial manner by which they adopt characteristic shapes, position themselves, and migrate with respect to time on these controlled scaffold geometries. Significant differences in these spatial outcomes for stem cell behavior were also observed to arise from changes in scaffold geometries. For example, a comparison of 0-45° versus 0-90° scaffold configurations according to an embodiment of the present invention showed stem cell positioning, shape, and migration that differed between the two scaffold geometries, demonstrating that the spatial characteristics of stem cells could be independently controlled solely via scaffold and bioreactor substrate geometries.

Figure 83:
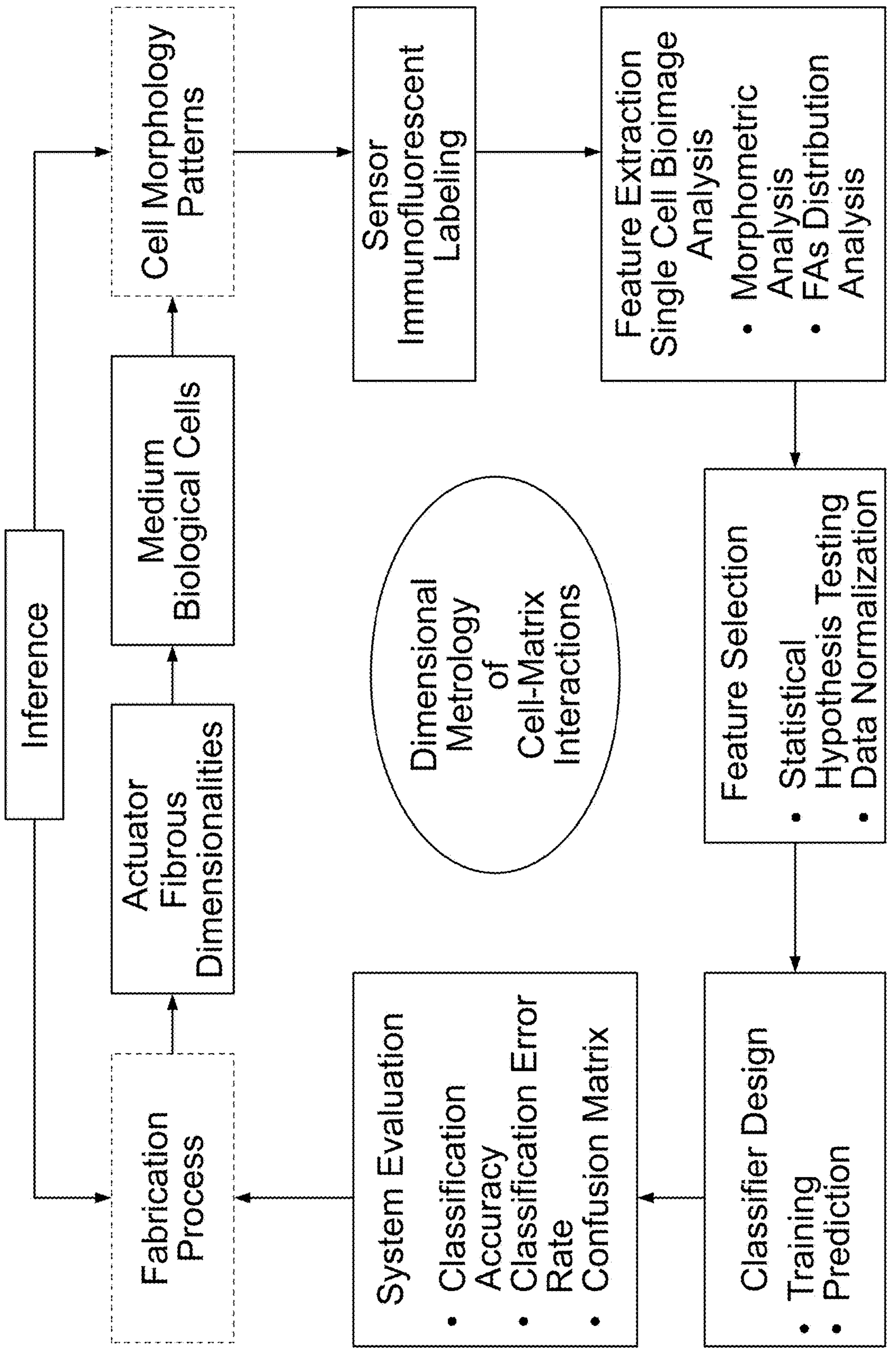
FIG. 83 is a schematic diagram providing an overview of a cell classification method according to an embodiment of the present invention.

Embodiments of the present invention include a method for quantitatively and reliably characterizing the measurements of cell position vectors and cell shapes. A block diagram of the metrology method is depicted in FIG. 83. Embodiments of the characterization method enable the rapid and reliable analysis and characterization of many cells under conditions of high throughput. Embodiments of the characterization method include immunofluorescent labeling of the cells for identification of structural and functional features with subsequent 3-D image acquisition, wherein the functional features include cell surface markers. Embodiments of the characterization method further include image analysis and automated algorithms for analyzing immunofluorescent-labeled cell features (FIG. 84), and generating statistics for the cell position and shape distributions that are then correlated with the stem cell phenotype. Embodiments of this method are referred to hereinafter as the "SIT" classification method. In embodiments of the present invention, the SIT classification method is integrated into an overall methodology of discovering the appropriate geometries for generating desirable cell shapes and phenotypes during the expansion of seeded cells.

In an embodiment of the present invention, images of a cell were generated via quantitative fluorescence confocal microscopy. Sample images appear in FIGS. 85-88, wherein a non-segmented view of a whole cell, a segmented view of just the cell body, a segmented view of just the nucleus body and a view displaying only the cell's focal adhesions are shown.

Figure 84:
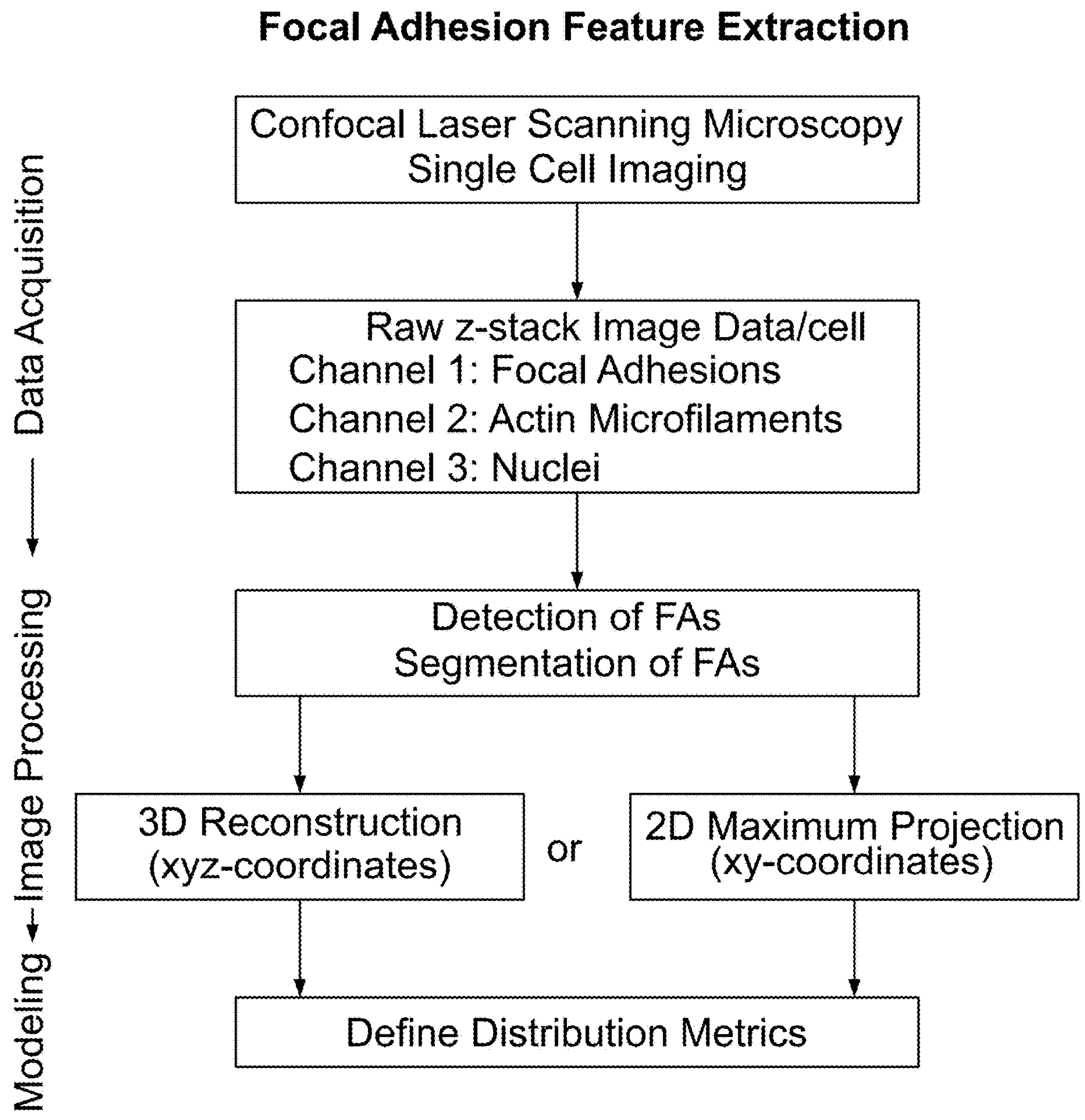
FIG. 84 is a flow diagram of a feature extraction algorithm in accordance with an embodiment of the present invention.
Figure 85:
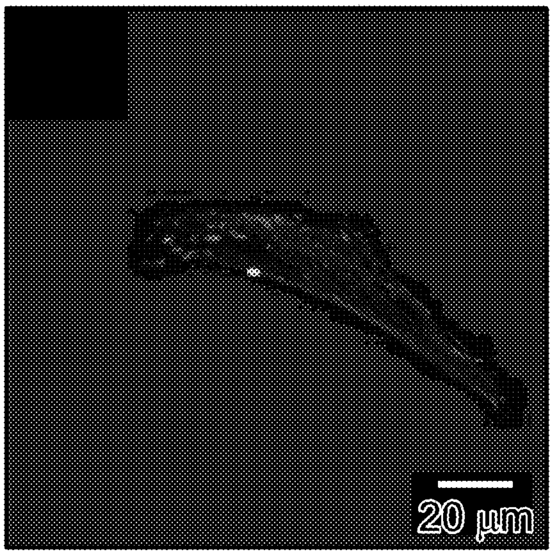
FIGS. 85-88 are a group of reproductions of photographic immunofluorescence images showing cellular structures observed during stem cell expansion according to a method of the present invention, wherein image FIG. 85 further is a colorized multi-channel maximum projection image obtained by combining three different single channel maximum projections, the single channel maximum projections obtained by processing Z-stack raw images, wherein the red channel is associated with the cytoskeleton, the blue channel is associated with the nucleus, and the green channel is associated with vinculin.
Figure 86:
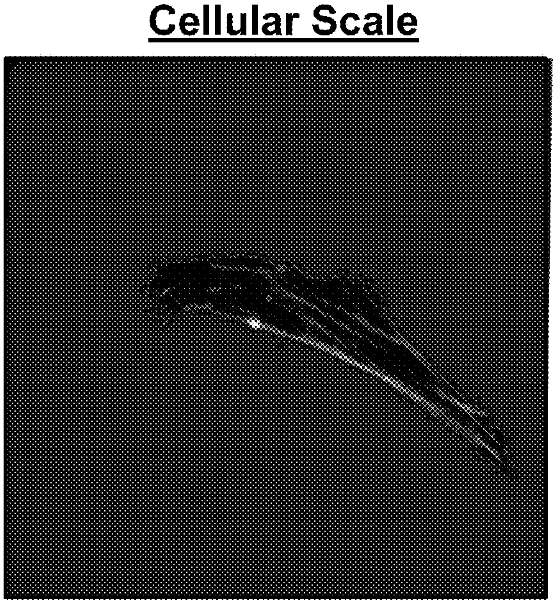
Figure 87:
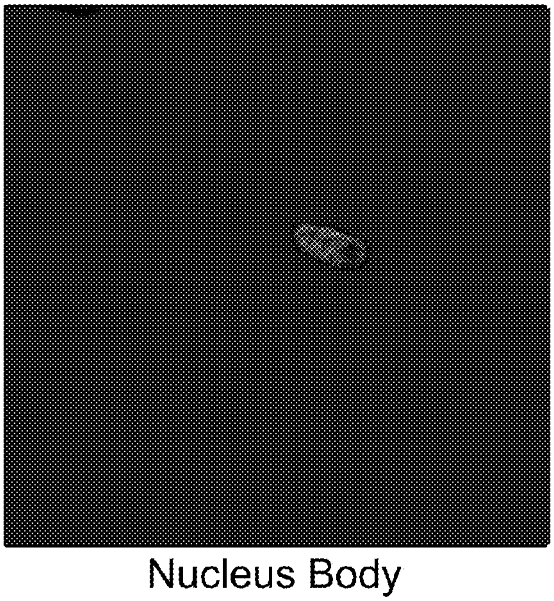
Figure 88:
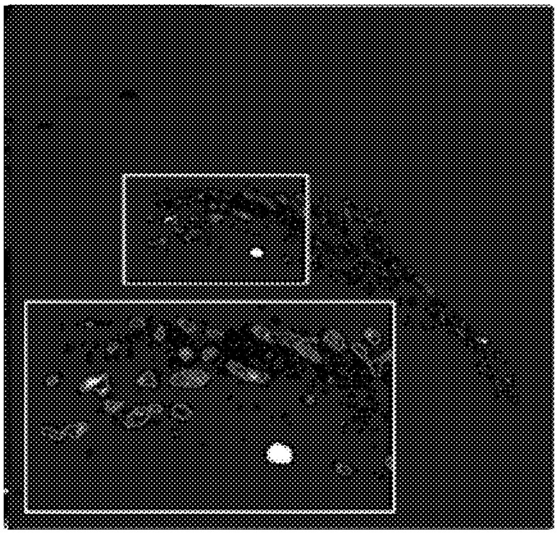
Figure 89:
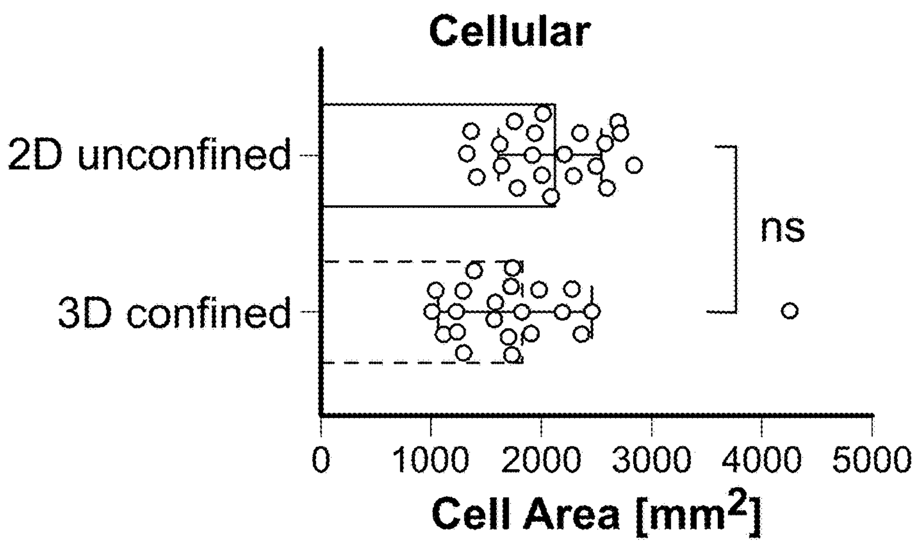
FIGS. 89-97 are a group of graphical illustrations of examples of a feature extraction procedure using single-cell automated bioimage analysis of immunofluorescent images according to a method of the present invention, providing a demonstration of the performance of an automated image processing algorithmic workflow according to an embodiment of the present invention that uses a representative cell cultured in 3-D microscale fibrous scaffold.
Figure 90:
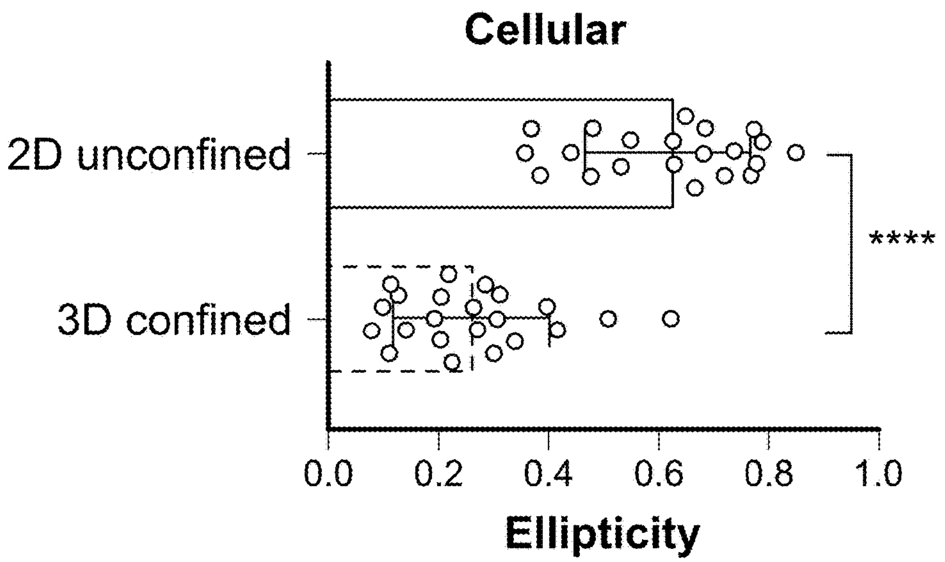
Figure 91:
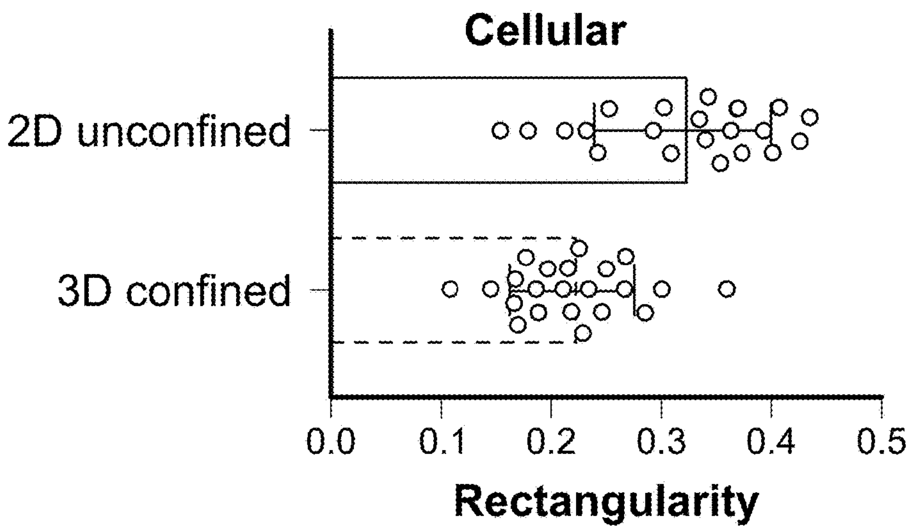
Figure 92:
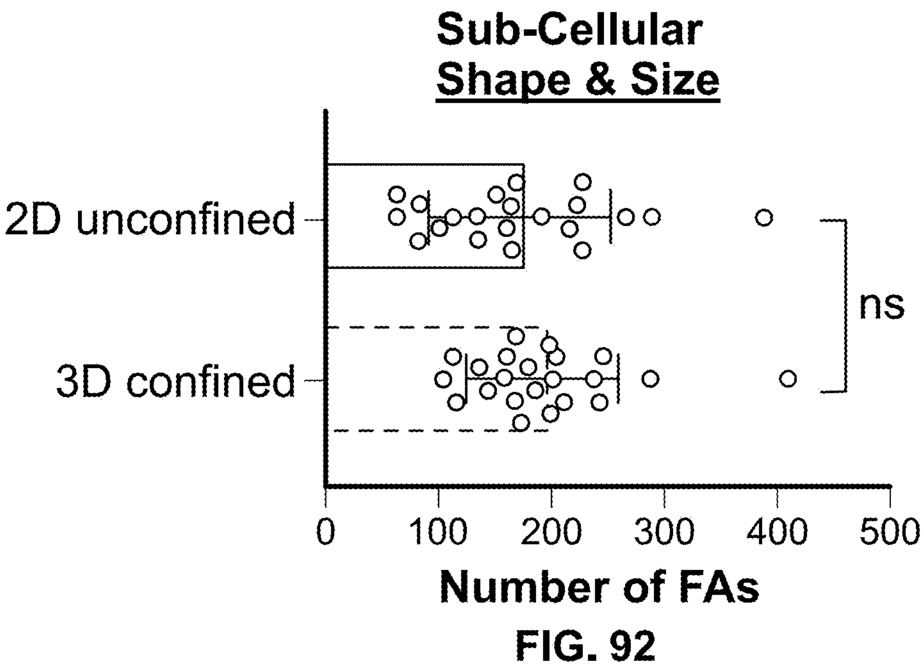
Figure 93:
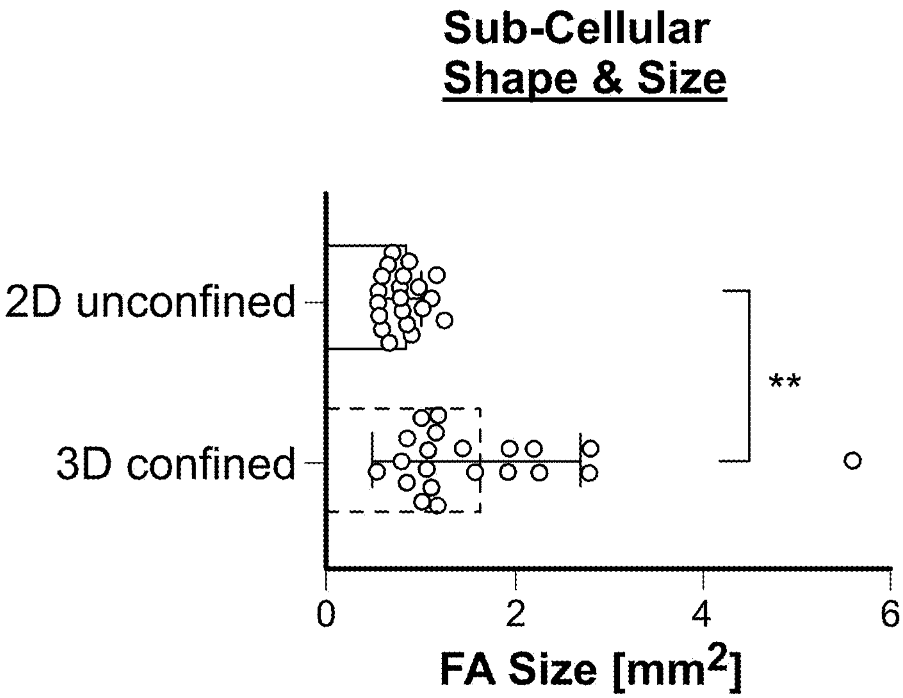
Figure 94:
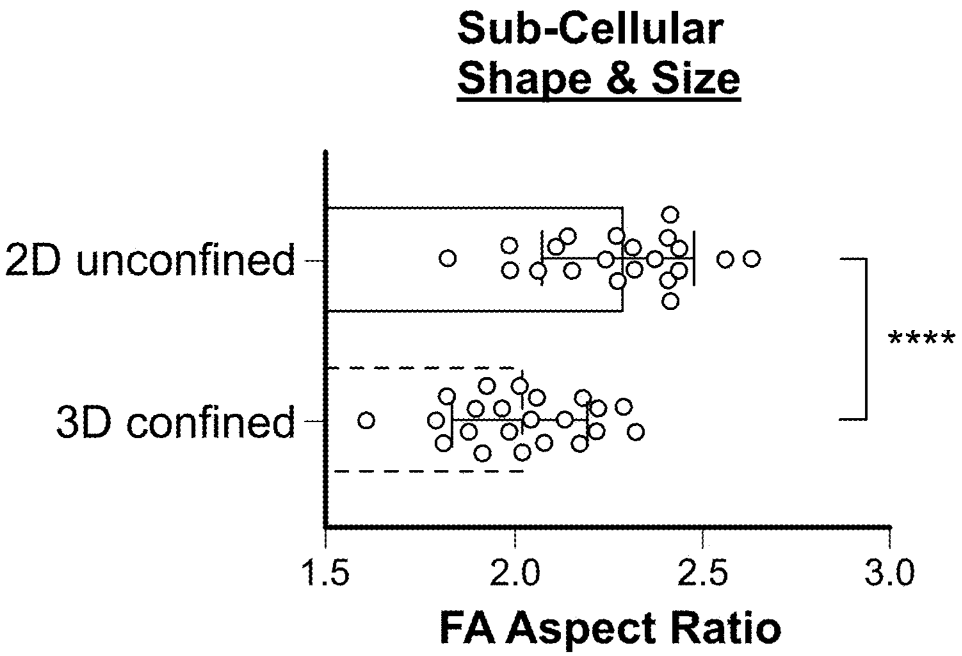
Figure 95:
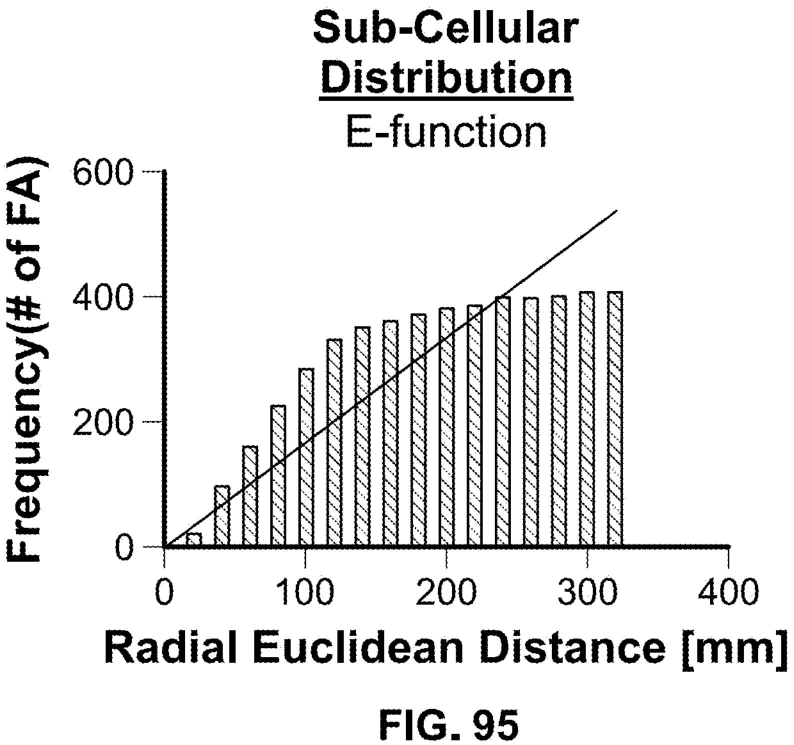
Figure 96:
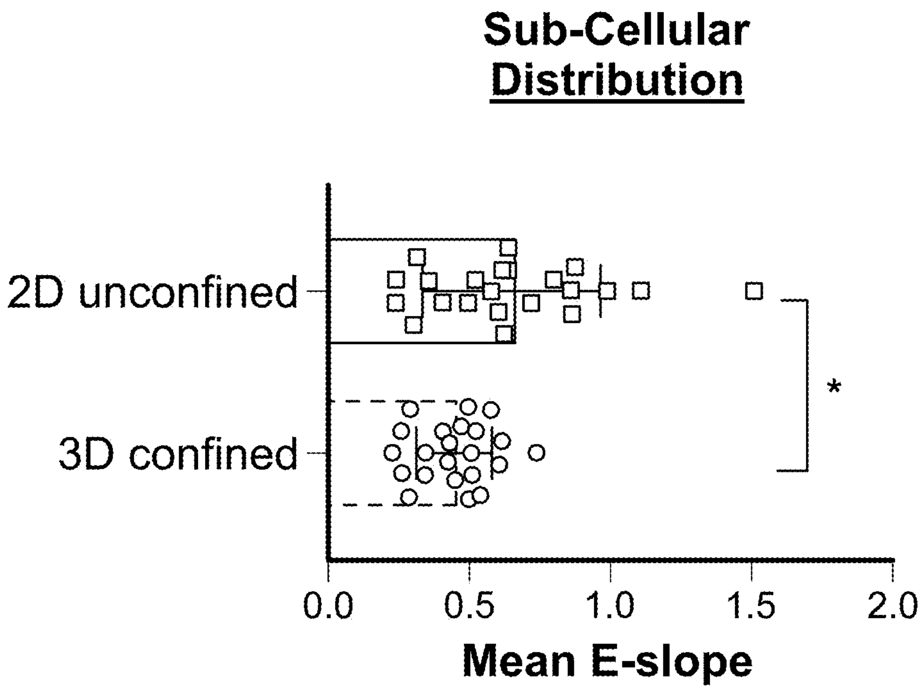
Figure 97:
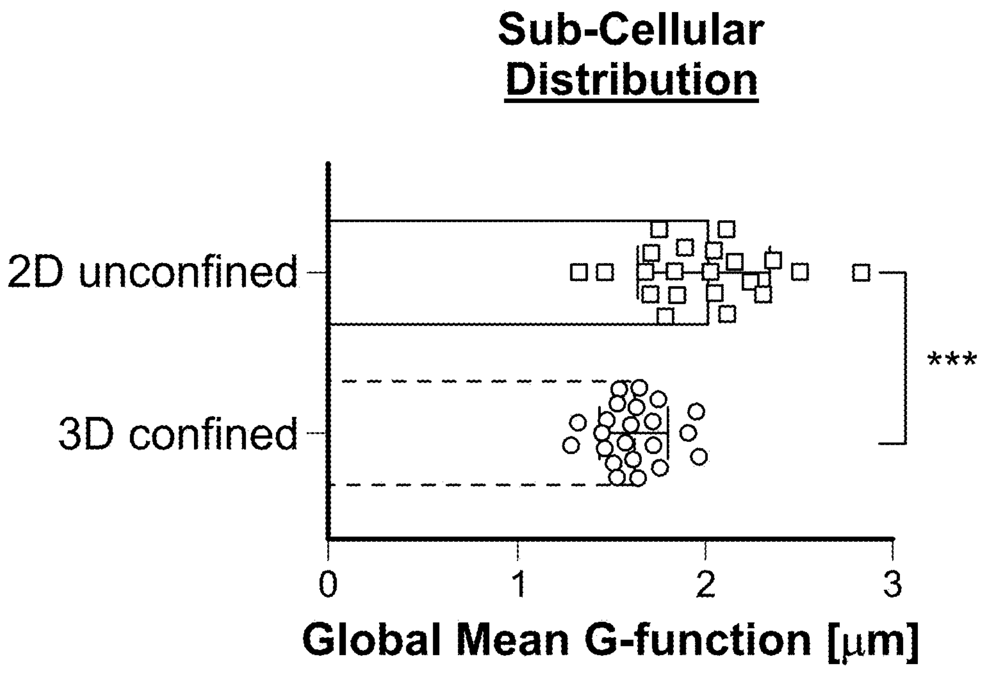
Figure 98:
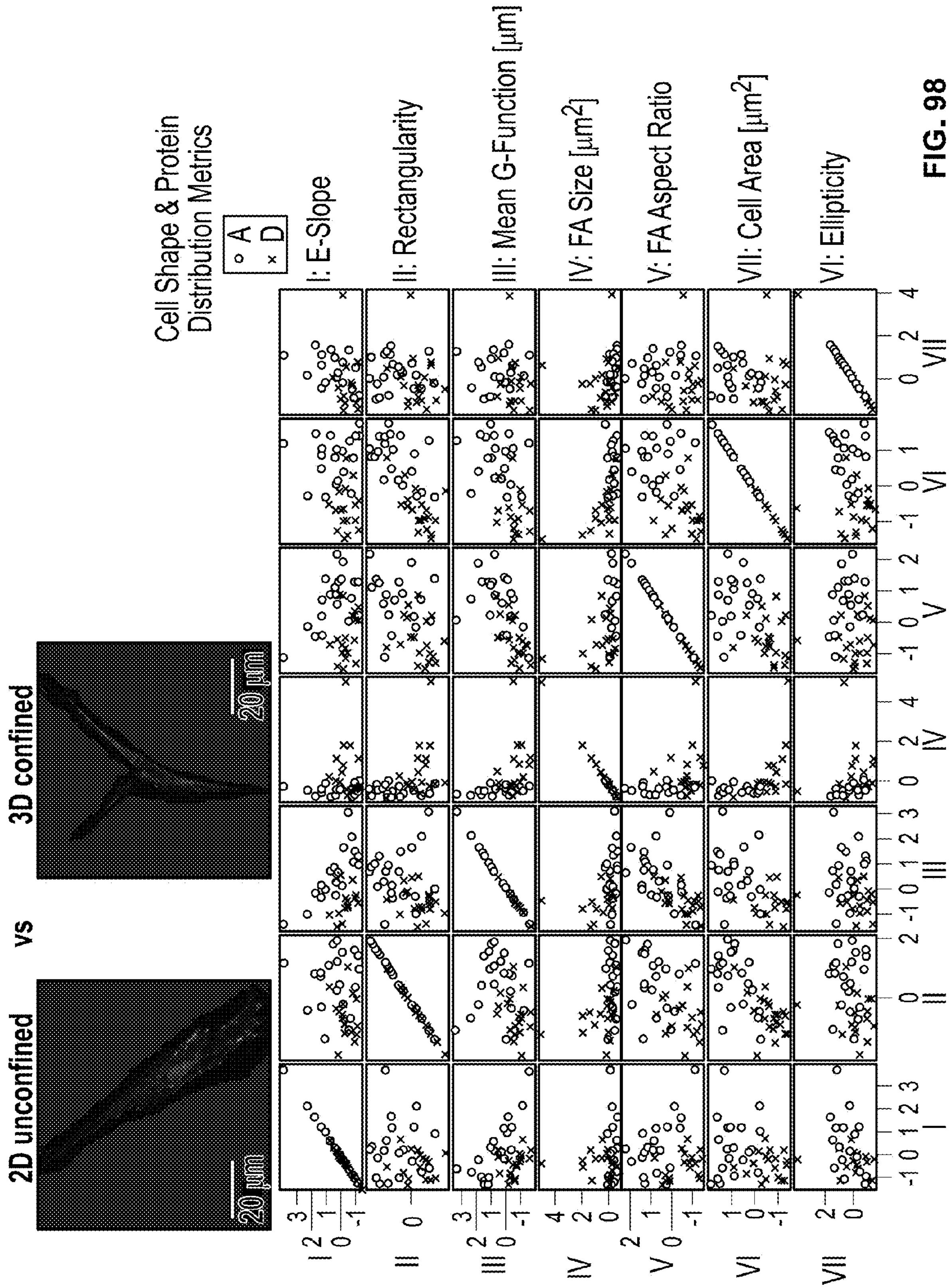
FIGS. 98-103 present graphical examples (FIGS. 98, 100 and 102) and confusion matrices (FIGS. 99, 101 and 103) illustrating the use of the classification methodology according to embodiments of the present invention to different scaffold geometries, and the confinement states of stem cells within the scaffolds during expansion, the graphical examples and confusion matrices documenting changes in cellular and subcellular adhesion proteins for the different geometries (for all cells under analysis>100), and demonstrating that the novel 3-D substrate architectures according to embodiments of the present invention induce uniform and geometry-dependent cell shapes and resulting phenotypes while, in contrast, the control stem cell cultures on flat surfaces or non-woven 2-D meshes with randomly oriented fibers induce heterogeneous cell shapes, presumably inducing phenotype heterogeneities.
Figure 99:
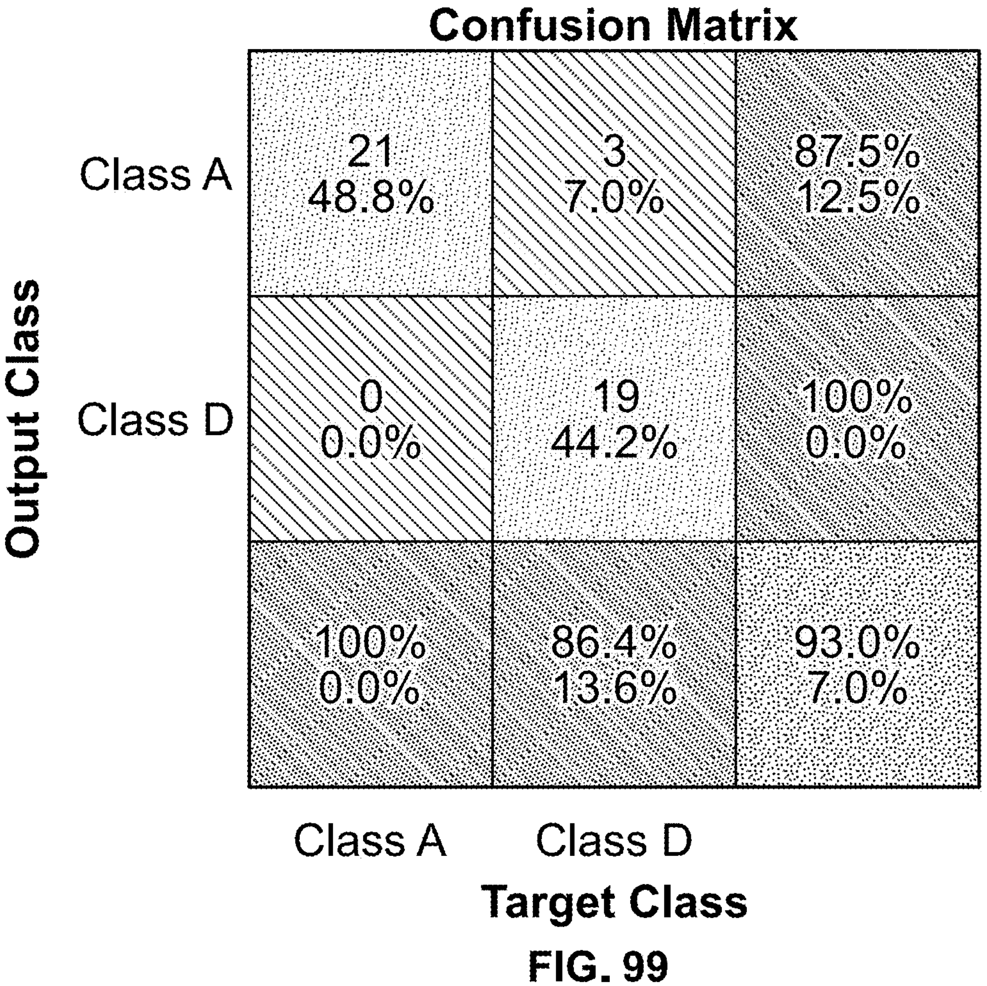

In an embodiment of the current invention, a FA metrology framework that allows the definition of metrics that model the distribution of the FA proteins at the cell level is disclosed. It can be understood as including three phases, as illustrated in FIG. 84.

First is the data acquisition phase, where the samples are images obtained with a high resolution confocal microscope equipped with 3 laser lines at 63× magnification and the samples are scanned across their thickness with a 0.1 μm step size. In this way, 3 sets of grayscale raw images can be produced for each cell, corresponding to the cellular and sub-cellular features of interest: FAs, Actin Microfilaments and Nuclei as depicted in FIGS. 85-88.

During the image processing phase, an algorithmic workflow where FAs can be automatically detected and segmented in each raw grayscale fluorescent image can be used, allowing for the 3-D volume reconstruction of all of the FAs within one cell in an xyz Cartesian coordinate system.

The image processing algorithmic procedure allows the development of critical cellular and subcellular focal adhesion morphometric and distribution metrics that are useful for the training and application of the developed classification method to various cell types according to an embodiment of the present invention. The results are depicted in FIGS. 89-97. During the modeling phase, metrics that describe the distribution characteristics of the proteins can be defined. The values of these metrics could possibly be FA-representative of the whole cell population within each sample.

In an embodiment, focal adhesions can be detected and segmented according to the algorithm. Initially the cell body is generated using thresholding and filtering techniques from a raw grayscale image colored green. Then, the individual FAs are detected and accurately segmented within the detected region of interest. Specifically, Clahe, which stands for "contrast limited adaptive histogram equalization," is used to equalize image brightness and contrast across the processed image.

In an embodiment, a thresholding step is performed, which automatically designates pixels as black or white based on whether they are above or below a certain pixel value.

In an embodiment, a dilation step is performed, wherein white pixels are removed if they are surrounded by a number of black pixels greater than or equal to the specified value.

In an embodiment, an erosion step is performed, wherein black pixels are removed in the same way as white pixels are removed in the dilation step.

In an embodiment, a reject features step is performed in which infinite areas corresponding to white or black pixels are removed.

In an embodiment, a Wiener filter is applied, which reduces the sparse noise while preserving edges In an embodiment, a fast Fourier transform is performed to reduce background noise and artifacts.

A manual review of the algorithm's output is advisable, to verify the accuracy of the algorithm.

Following the same image processing algorithmic workflow for not only the FA channel, but also for the Actin Microfilament and DAPI channel allows for the 3-D volume reconstruction of each feature. They can then be merged into a composite image for visual inspection.

Two metrics were developed for the SIT algorithm. In particular, the radial Euclidean distances between focal adhesion and nuclei centroids were recorded for both a 2-D petri dish control and a 3-D confined and suspended state (i.e., 0-45° scaffold) system. Frequency distribution modeling was performed based on the Euclidean distance. A function was developed to characterize the relationship between radial Euclidean distances and the frequency of FAs within such a distance. From this E-function the slope was taken as the E-slope parameter. An increase in this E-slope parameter correlates with the formation of more FAs closer to the nucleus.

A similar frequency distribution modeling was also performed with the distance from each focal adhesion to its closest neighbor. A G-function was generated based on the relationship between nearest neighbor distance and the frequency of focal adhesions in this range. A smaller G-function value correlates with a more aggregated FA pattern at the individual/single cell level.

A morphometric analysis found that FA number and total area of FAs were not statistically significant when comparing melt electrospinning writing scaffolds with conventional controls (i.e., randomly electrospun meshes and a glass medium). However, FA size was higher for the MEW scaffold. Additionally the aspect ratio of the FAs in this experiment correlated with the ellipticity of the cell shape.

It was also found that cell area had no statistical differences between the four conditions, though the random fibrous substrates did have greater solidity. This is believed to be due to these fibers introducing random candidate cell attachment, resulting in more ruffled cell-shapes. Meanwhile 0-45° MEW-printed scaffolds saw triangular cell shapes with distinct cell attachment points. Thus, the MEW embodiment saw lower rectangularity and ellipticity.

A 7-D Cartesian coordinate system of cell shape phenotypes, in which each axis represents a feature metric, was developed for the 7 metrics computed from the Morphometric described above. a) Global (over a population of cells) E-slope (“I”), b) Rectangularity (“II”), c) Global (over a population of cells) mean G-function (“III”), d) FA size (“IV”), e) FA Aspect Ratio (“V”), f) Ellipticity (“VI”), g) Cell Area (“VII”) were chosen as the seven, dimensional parameters. Within this representation, each point represents one single cell feature-vector with 7 elements corresponding to the computed metrics for the specific cell. All metrics are normalized using a Z-score function, which centers and scales all metric values to have zero mean and unit standard deviation, respectively. The transformed metric vectors for each cell population are multidimensional datasets to train a Support Vector Machine (SVM) with a linear kernel using the classification learner package in MATLAB. The linear-kernel SVM is a supervised machine learning algorithm that can classify the data by finding the best hyperplane that separates all data points into: a) a class representing cells being in a 2-D unconfined state (Class A) and b) a class representing cells being in a 3-D confined state (class D). The best hyperplane for the SVM algorithm is considered the one with the largest margin between the two classes with the margin being the maximum width of the slab parallel to the hyperplane that has no interior data points. The predictive accuracy of the linear-kernel SVM can be assessed using a 5-fold cross-validation scheme to protect against overfitting. Here, the data are randomly partitioned in 5 folds where, for each fold, the scheme trains the linear SVM using the out-of-fold observations and assesses the model performance using the in-fold data. The classification accuracy is defined as the average percentage of the correctly classified data for each fold and used as a metric for the classifier's predictive performance.

The results of the machine learning task, which is the classification of cell shape phenotypes modeled for every scaffold are depicted in FIGS. 98-103. While the initial assessment of the discriminatory information of each metric provides valuable insights concerning the cell shape phenotypic differences across and within each cell population group, the ability to infer the substrate dimensionality and architecture directly from single cell morphologies remains to be validated. To accomplish that, the single-cell multi-dimensional data sets are used to train the chosen machine learning algorithm with the aim of distinguishing between four different classes by considering all features simultaneously. The class declaration is depicted in Table 5 below, where all substrate dimensionalities and topographies are depicted along with the cell confinement states:

TABLE 5

| Class | Substrate Dimensionality - Architecture (METROLOGY- FIGS. 12 AND 13) | Cell Confinement State (OBSERVATIONS) |
|---|---|---|
| A | 2-D uniform (Controls - Glass surfaces) | unconfined |
| B | random (SES - 1 min) | confined |
| C | random (SES - 3 min) | confined |
| D | 3-D uniform (MEW \| 0-45°) | confined |

Figure 100:
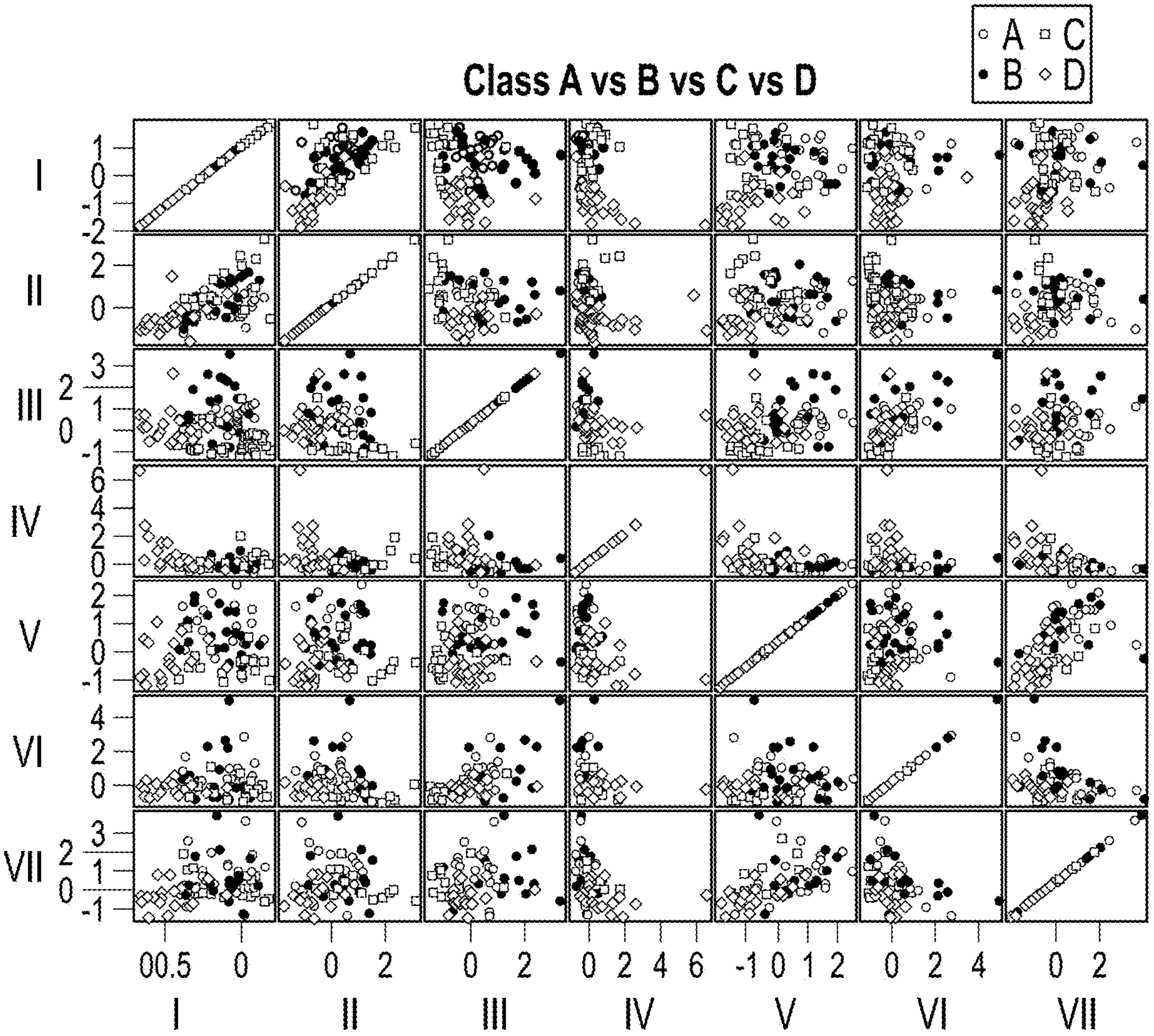
Figure 101:
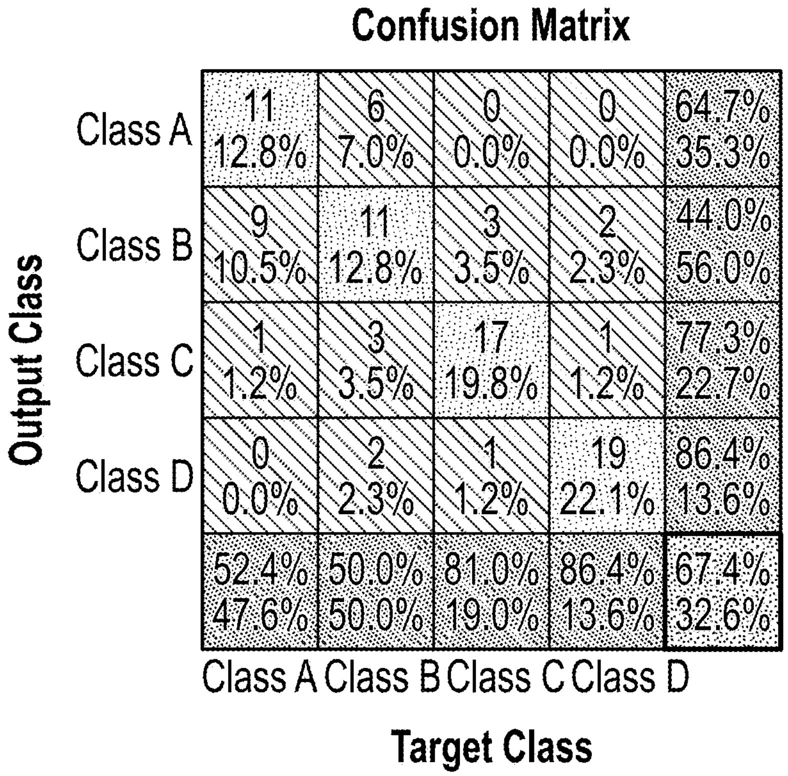
Figure 103:
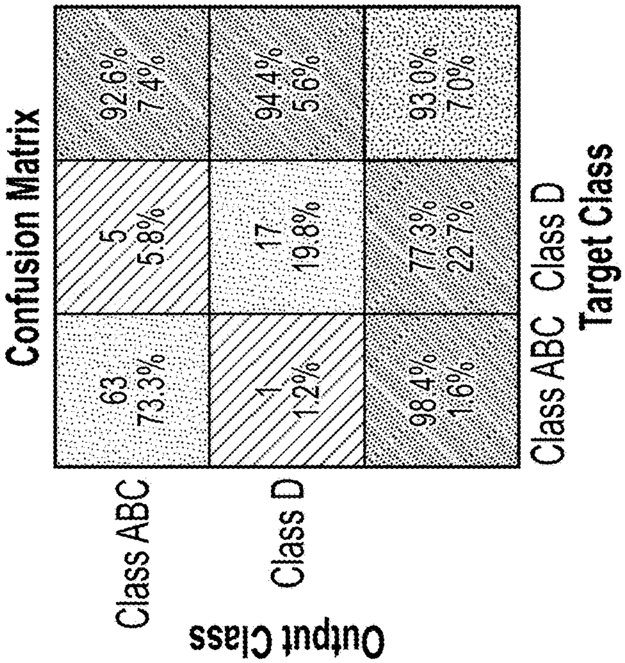
Figure 102:
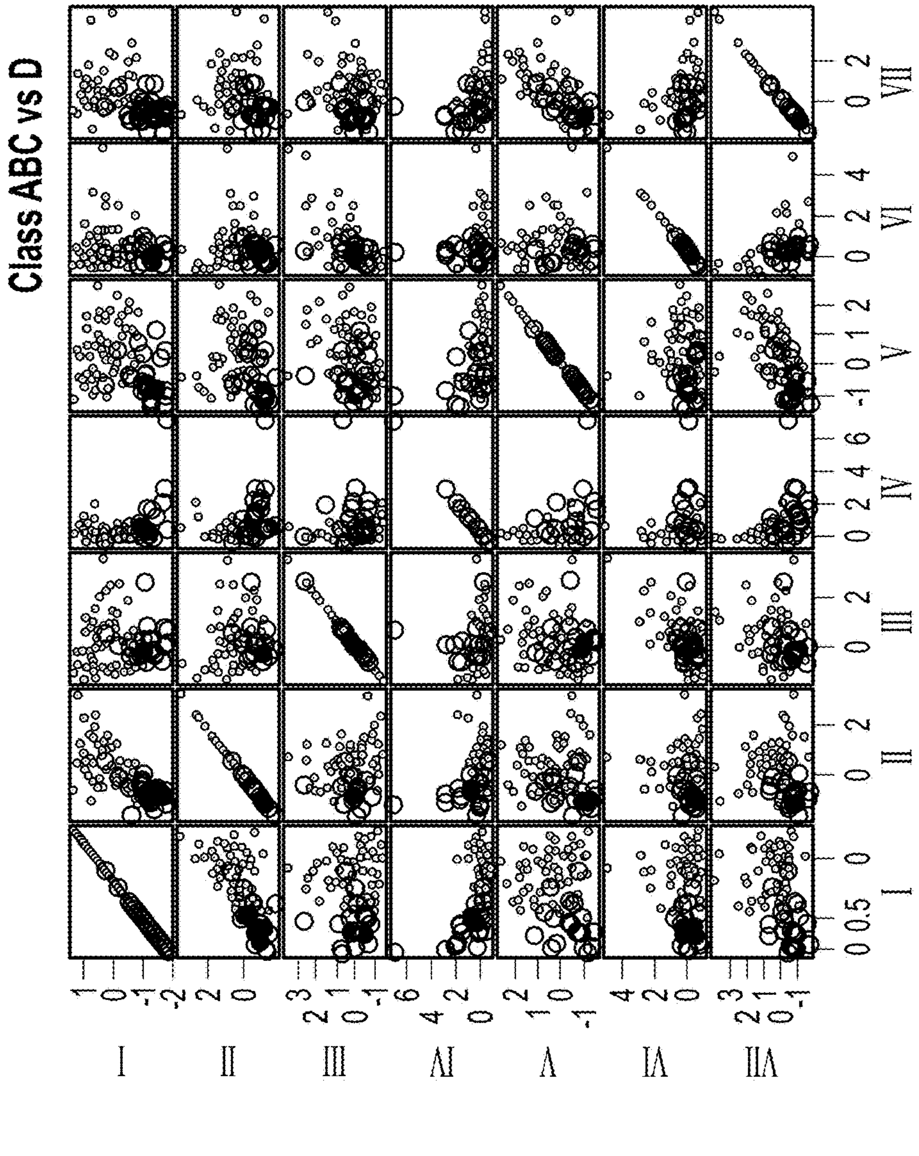

Three different classification tasks are performed. Combinations of the scaled metrics are plotted to allow easier assessment of the results (FIGS. 98-103). The capability of the classifier to operate satisfactorily with data outside the training set for each classification task is assessed based on the classification accuracy. Initially, the multi-class classification problem is attempted by taking into account cell morphologies across all the fabricated substrates (FIGS. 100 and 101). The classifier demonstrates a low classification accuracy (67%), which can be explained by the large intra-class variance of Class B. By removing Class B, the classification accuracy increases to 90.6%, demonstrating that the trained classifier can predict with high accuracy the substrate from which a cell originates based strictly on its feature vector identity. Remarkably, when the binary classification task is run by combining all classes corresponding to the flat or electrospun SES substrates, including the “noisy” Class B against Class D, the classification accuracy level remains around 93%. Thus, it is demonstrated that the 3-D microscale precision-stacked substrates promote a confined and suspended state that morphologically stands out both at the cellular as well as the sub-cellular FA level.

It is concluded that the MEW substrates may promote less migratory early cell shape phenotypic responses that are characteristic of a confined and suspended state. These responses are distinct from the confinement states adopted by the more actively motile cells on the flat and electrospun SES substrates. In the former case, cells tend to develop a more aggregated pattern of larger and less elongated mature FAs within cell bodies. The global shapes of the cells are dictated by the substrate's triangular porous microarchitecture. In the latter case, cells tend to develop a more dispersed pattern of mature FAs within more elliptic cell bodies. Across the 2-D substrates, the degree of the resultant cell confinement appears to be regulated by the extent of fiber coverage with the cells on the controls substrate (0% of fiber coverage) being in an unconfined state. Lastly, the substrates' structural heterogeneity with respect to fiber diameter and pore size distribution dictates the variance of the defined morphometric and protein distribution metrics with the MEW|0-45° and SES-3 min substrate demonstrating the most and least homogeneous population of single cell morphologies, respectively.

Figure 104:
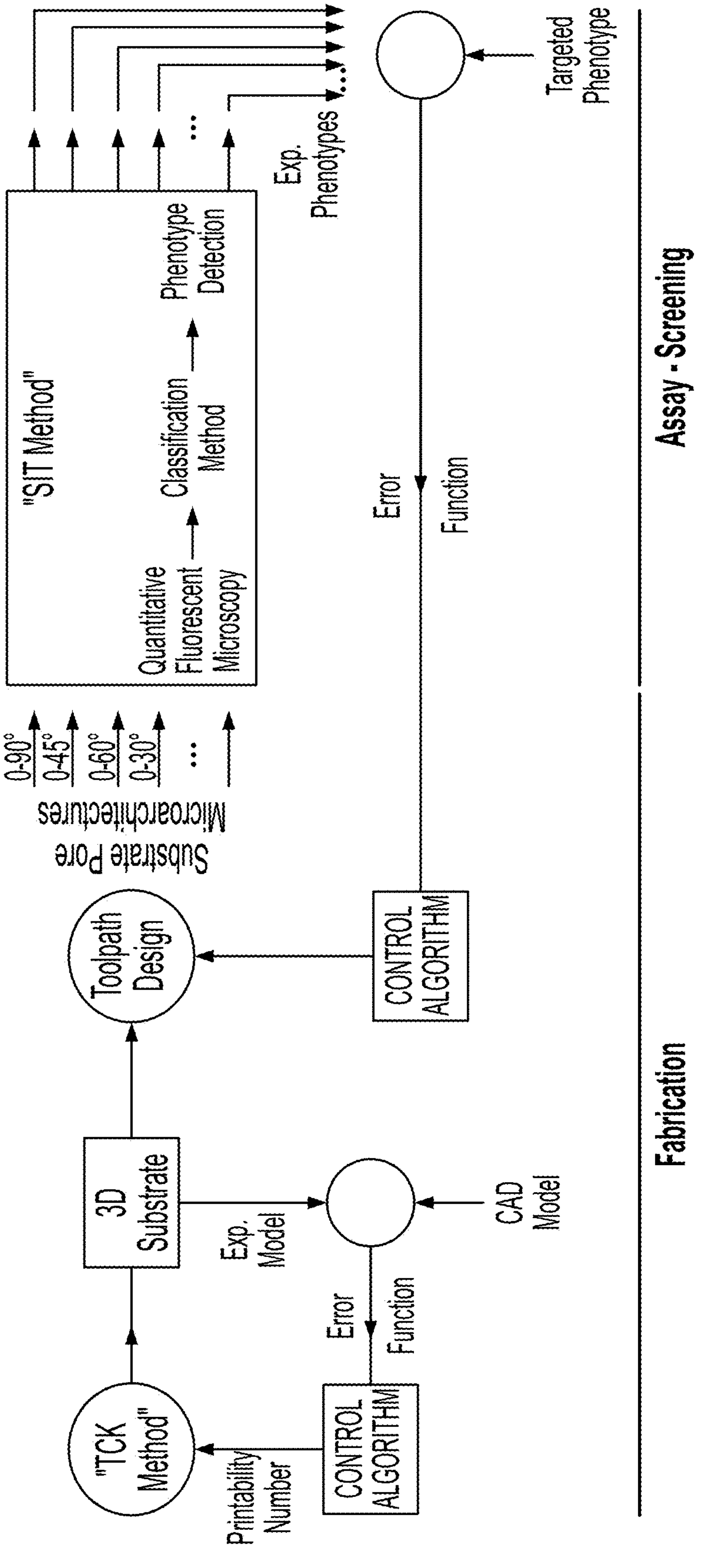
FIG. 104 is a schematic diagram of a concept for industrial exploitation of the classification method according to an embodiment of the present invention, further including feedback and feedforward control methodologies for the programmable expansion and harvesting of stem cells having phenotypes that are targeted and realized according to a method of the present invention.

Integration of embodiments of the TCK fabrication method and embodiments of the SIT classification scheme enable discovery of the extent and time duration over which stem cells conserve their shapes and phenotypes, thereby facilitating manipulation of the shapes and phenotypes of the stem cells using the geometry of the scaffold or the bioreactor substrate as a tool. A schematic diagram of a concept for industrial exploitation of the classification method according to an embodiment of the present invention, further including feedback and feedforward control methodologies for the programmable expansion and harvesting of stem cells having phenotypes that are targeted and realized according to a method of the present invention is depicted in FIG. 104. By such means, stem cell therapies can be improved significantly by tailoring the geometries of scaffolds and bioreactors used during the administration of such therapies.

It will be understood that the embodiments described herein are merely exemplary and that a person of ordinary skill in the art may make many variations and modifications without departing from the spirit and scope of the invention. All such variations and modifications are intended to be included within the scope of the invention as disclosed, including any and all such variations and modifications disclosed in *Melt Electrospinning Writing Process Guided by a "Printability Number*," published in the Journal of Manufacturing Science and Engineering, August 2017, Vol. 139, pgs. 081004-1 to 081004-15, the contents of which are incorporated herein in their entireties.

We claim:

1. A three-dimensional scaffold, comprising a porous triangular microarchitecture having a 0-90 degree or 0-45 degree pore structure provided by a plurality of woven porous substrates stacked on each other, the porous microarchitecture having geometrical feature sizes of about 100 microns or smaller, and each of the woven porous substrates comprising a plurality of polycaprolactone fibers that are interwoven together.

2. The three-dimensional scaffold of claim 1, the porous triangular microarchitecture comprising a plurality of triangular pores that are substantially uniform in size and shape.

3. The three-dimensional scaffold of claim 1, the plurality of woven porous substrates being fabricated from a polycaprolactone melt using a melt electrowriting technique.

4. The three-dimensional scaffold of claim 1, the plurality of woven porous substrates being fabricated by melt electrowriting.

5. The three-dimensional scaffold of claim 1, the geometrical feature sizes being 10-100 μm.

6. The three-dimensional scaffold of claim 1, the plurality of fibers having a submicron diameter.

7. The three-dimensional scaffold of claim 1, the porous microarchitecture having a 0-45-135-90 degree pore structure.

8. A method of expanding cells in vitro, comprising:

providing the three-dimensional scaffold of claim 1, seeding a plurality of cells on the three-dimensional scaffold, culturing the cells to obtain expanded cells that are substantially uniform in shape and phenotype.

9. The method of claim 8, wherein the cells are stem cells and the expanded cells maintain stemness.

10. The method of claim 8, wherein the expanded cells are homogenous.

11. The method of claim 8, further comprising determining a relationship between the porous microarchitecture and the shape and phenotype of the expanded cells.

12. The method of claim 8, further comprising generating a metrology framework that models and classifies cell confinement states for various porous microarchitectures.

13. The method of claim 8, further comprising classifying cell shapes and/or focal adhesions using machine learning.

14. The method of claim 13, wherein the machine learning is carried out using immunofluorescent imaging of the expanded cells.

15. The method of claim 13, wherein the immunofluorescent imaging comprises immunofluorescent labeling of positive and/or negative cell surface markers.

16. The method of claim 8, further comprising tuning so as to reproducibly harvesting targeted cell populations.

* * * * *